(12) United States Patent
Taheri et al.

(10) Patent No.: US 11,883,636 B2
(45) Date of Patent: Jan. 30, 2024

(54) SYRINGE PLUNGER ENGAGEMENT MECHANISM

(71) Applicant: BAYER HEALTHCARE LLC, Whippany, NJ (US)

(72) Inventors: Shahab Taheri, The Ponds (AU); Timothy Newing, Thornleigh (AU); Grant Karsten, Carlingford (AU); Aiden Salm, Oakville (AU); Han Min Thu, Mandalay (MM)

(73) Assignee: BAYER HEALTHCARE LLC, Whippany, NJ (US)

( * ) Notice: Subject to any disclaimer, the term of this patent is extended or adjusted under 35 U.S.C. 154(b) by 798 days.

(21) Appl. No.: 16/975,944

(22) PCT Filed: Feb. 25, 2019

(86) PCT No.: PCT/US2019/019360
§ 371 (c)(1),
(2) Date: Aug. 26, 2020

(87) PCT Pub. No.: WO2019/168776
PCT Pub. Date: Sep. 6, 2019

(65) Prior Publication Data
US 2020/0405972 A1 Dec. 31, 2020

Related U.S. Application Data

(60) Provisional application No. 62/635,669, filed on Feb. 27, 2018.

(51) Int. Cl.
*A61M 5/315* (2006.01)

(52) U.S. Cl.
CPC .... *A61M 5/31581* (2013.01); *A61M 5/31513* (2013.01); *A61M 5/31515* (2013.01)

(58) Field of Classification Search
CPC .......... A61M 5/31581; A61M 5/31513; A61M 5/31515
See application file for complete search history.

(56) References Cited

U.S. PATENT DOCUMENTS

| | | | |
|---|---|---|---|
| 1,265,537 | A | 5/1918 | Ivan |
| 1,687,323 | A | 10/1928 | Cook |

(Continued)

FOREIGN PATENT DOCUMENTS

| | | |
|---|---|---|
| AU | 317487 | 1/2008 |
| DE | 2919978 A1 | 11/1980 |

(Continued)

OTHER PUBLICATIONS

Brochure for "Angiomat 6000" of Liebel-Farsheim, 2111 E. Galbraith Road, Cincinnati, OH 45215, @ 1987.

(Continued)

*Primary Examiner* — Bradley J Osinski
(74) *Attorney, Agent, or Firm* — Joseph L. Kent; James R. Stevenson; David Schramm

(57) ABSTRACT

A fluid injector system has at least one reciprocally operable piston having a piston head, and a plunger engagement mechanism associated with the piston head. The plunger engagement mechanism has a cam sleeve disposed within the piston head and movable relative to the piston head, the cam sleeve having one or more tracks defining a cam surface. The plunger engagement mechanism further has an actuator operatively connected to the cam sleeve for moving the cam sleeve relative to the piston head, and one or more pins disposed within the cam sleeve. The one or more pins are movable within the one or more tracks with movement of the cam sleeve between a first or withdrawn position, wherein the one or more pins are radially withdrawn into the piston head and a second or extended position, wherein the (Continued)

one or more pins protrude radially outward relative to an outer surface of the piston head.

20 Claims, 13 Drawing Sheets

(56) References Cited

U.S. PATENT DOCUMENTS

| | | |
|---|---|---|
| 1,988,480 A | 1/1935 | Campkin |
| 2,392,196 A | 1/1946 | Smith |
| 2,419,401 A | 4/1947 | Hinds |
| 2,702,547 A | 2/1955 | Glass |
| 2,842,126 A | 7/1958 | Brown |
| 3,051,173 A | 8/1962 | Johnson et al. |
| D203,730 S | 2/1966 | Porat |
| 3,270,483 A | 9/1966 | Smoyer et al. |
| 3,348,545 A | 10/1967 | Sarnoff et al. |
| 3,468,471 A | 9/1969 | Linder |
| 3,604,417 A | 9/1971 | Stolzenberg et al. |
| 3,623,474 A | 11/1971 | Heilman et al. |
| 3,645,262 A | 2/1972 | Harrigan |
| 3,701,345 A | 10/1972 | Heilman |
| 3,705,582 A | 12/1972 | Stumpf et al. |
| 3,720,211 A | 3/1973 | Kyrias |
| 3,738,539 A | 6/1973 | Beich |
| 3,752,145 A | 8/1973 | Runnells et al. |
| 3,796,218 A | 3/1974 | Burke et al. |
| 3,809,082 A | 5/1974 | Hurschman |
| 3,812,843 A | 5/1974 | Wootten et al. |
| 3,902,491 A | 9/1975 | Lajus |
| 3,964,139 A | 6/1976 | Kleinmann et al. |
| 3,987,940 A | 10/1976 | Tischlinger |
| 3,998,224 A | 12/1976 | Chiquiar-Arias |
| 4,006,736 A | 2/1977 | Kranys et al. |
| 4,030,498 A | 6/1977 | Tompkins |
| 4,080,967 A | 3/1978 | O'Leary |
| 4,148,316 A | 4/1979 | Xanthopoulos |
| 4,155,490 A | 5/1979 | Glenn |
| 4,159,713 A | 7/1979 | Prais |
| 4,180,006 A | 12/1979 | Ross |
| 4,180,069 A | 12/1979 | Walters |
| 4,226,236 A | 10/1980 | Genese |
| 4,252,118 A | 2/1981 | Richard et al. |
| 4,278,086 A | 7/1981 | Hodgins et al. |
| 4,303,070 A | 12/1981 | Ichikawa et al. |
| 4,345,595 A | 8/1982 | Whitney et al. |
| 4,351,332 A | 9/1982 | Whitney et al. |
| 4,356,822 A | 11/1982 | Winstead-Hall |
| 4,424,720 A | 1/1984 | Bucchianeri |
| 4,452,251 A | 6/1984 | Heilman |
| 4,453,934 A | 6/1984 | Gahwiler et al. |
| 4,464,265 A | 8/1984 | Joyner |
| 4,465,472 A | 8/1984 | Urbaniak |
| 4,465,473 A | 8/1984 | Ruegg |
| 4,475,666 A | 10/1984 | Bilbrey et al. |
| 4,476,381 A | 10/1984 | Rubin |
| 4,490,256 A | 12/1984 | Nussbaumer et al. |
| 4,493,646 A | 1/1985 | Lacour et al. |
| 4,500,310 A | 2/1985 | Christinger |
| 4,529,401 A | 7/1985 | Leslie et al. |
| 4,562,844 A | 1/1986 | Carpenter et al. |
| 4,568,335 A | 2/1986 | Updike et al. |
| 4,573,978 A | 3/1986 | Reilly |
| 4,585,439 A | 4/1986 | Michel |
| 4,604,847 A | 8/1986 | Moulding, Jr. et al. |
| 4,612,010 A | 9/1986 | Hamacher et al. |
| 4,617,016 A | 10/1986 | Blomberg |
| 4,628,969 A | 12/1986 | Jurgens, Jr. et al. |
| 4,636,198 A | 1/1987 | Stade |
| 4,648,872 A | 3/1987 | Kamen |
| 4,650,475 A | 3/1987 | Smith et al. |
| 4,652,260 A | 3/1987 | Fenton, Jr. et al. |
| 4,664,128 A | 5/1987 | Lee |
| 4,676,776 A | 6/1987 | Howson |
| 4,677,980 A | 7/1987 | Reilly et al. |
| 4,677,981 A | 7/1987 | Coursant |
| 4,681,566 A | 7/1987 | Fenton, Jr. et al. |
| 4,685,903 A | 8/1987 | Cable et al. |
| 4,695,271 A | 9/1987 | Goethel |
| 4,705,509 A | 11/1987 | Stade |
| 4,718,463 A | 1/1988 | Jurgens, Jr. et al. |
| 4,722,734 A | 2/1988 | Kolln |
| 4,741,732 A | 5/1988 | Crankshaw et al. |
| 4,741,736 A | 5/1988 | Brown |
| 4,749,109 A | 6/1988 | Kamen |
| 4,755,172 A | 7/1988 | Baldwin |
| 4,767,406 A | 8/1988 | Wadham et al. |
| 4,773,900 A | 9/1988 | Cochran |
| 4,838,857 A | 6/1989 | Strowe et al. |
| 4,840,616 A | 6/1989 | Banks |
| 4,842,581 A | 6/1989 | Davis |
| RE32,974 E | 7/1989 | Porat et al. |
| 4,852,768 A | 8/1989 | Bartsch |
| 4,853,521 A | 8/1989 | Claeys et al. |
| 4,854,324 A | 8/1989 | Hirschman et al. |
| 4,863,427 A | 9/1989 | Cocchi |
| 4,869,720 A | 9/1989 | Chernack |
| 4,878,896 A | 11/1989 | Garrison et al. |
| 4,908,022 A | 3/1990 | Haber |
| 4,911,695 A | 3/1990 | Lindner |
| 4,923,443 A | 5/1990 | Greenwood et al. |
| 4,929,238 A | 5/1990 | Baum |
| 4,931,043 A | 6/1990 | Ray et al. |
| 4,932,941 A | 6/1990 | Min et al. |
| 4,936,833 A | 6/1990 | Sams |
| 4,943,279 A | 7/1990 | Samiotes et al. |
| 4,950,243 A | 8/1990 | Estruch |
| 4,966,601 A | 10/1990 | Draenert |
| 4,969,874 A | 11/1990 | Michel et al. |
| 4,973,309 A | 11/1990 | Sultan |
| 4,978,335 A | 12/1990 | Arthur |
| 4,988,337 A | 1/1991 | Ito |
| 4,997,423 A | 3/1991 | Okuda et al. |
| 5,000,735 A | 3/1991 | Whelan |
| 5,007,904 A | 4/1991 | Densmore et al. |
| 5,019,045 A | 5/1991 | Lee |
| 5,024,663 A | 6/1991 | Yum |
| 5,033,650 A | 7/1991 | Colin et al. |
| 5,034,004 A | 7/1991 | Crankshaw |
| 5,047,014 A | 9/1991 | Mosebach et al. |
| 5,059,179 A | 10/1991 | Quatrochi et al. |
| 5,062,832 A | 11/1991 | Seghi |
| 5,078,683 A | 1/1992 | Sancoff et al. |
| 5,084,017 A | 1/1992 | Maffetone |
| 5,085,638 A | 2/1992 | Farbstein et al. |
| 5,085,643 A | 2/1992 | Larkin et al. |
| 5,090,962 A | 2/1992 | Landry, Jr. et al. |
| 5,093,079 A | 3/1992 | Bakaitis et al. |
| 5,094,148 A | 3/1992 | Haber et al. |
| 5,104,374 A | 4/1992 | Bishko et al. |
| 5,106,372 A | 4/1992 | Ranford |
| 5,106,379 A | 4/1992 | Leap |
| 5,122,118 A | 6/1992 | Haber et al. |
| 5,135,507 A | 8/1992 | Haber et al. |
| 5,147,311 A | 9/1992 | Pickhard |
| 5,153,827 A | 10/1992 | Coutre et al. |
| 5,176,642 A | 1/1993 | Clement |
| 5,181,912 A | 1/1993 | Hammett |
| 5,226,897 A | 7/1993 | Nevens et al. |
| 5,236,416 A | 8/1993 | McDaniel et al. |
| 5,242,408 A | 9/1993 | Jhuboo et al. |
| 5,246,423 A | 9/1993 | Farkas |
| 5,254,086 A | 10/1993 | Palmer et al. |
| 5,254,101 A | 10/1993 | Trombley, III |
| 5,256,154 A | 10/1993 | Liebert et al. |
| 5,256,157 A | 10/1993 | Samiotes et al. |
| 5,269,762 A | 12/1993 | Armbruster et al. |
| 5,275,582 A | 1/1994 | Wimmer |
| 5,279,569 A | 1/1994 | Neer et al. |
| 5,282,792 A | 2/1994 | Imbert |
| 5,282,858 A | 2/1994 | Bisch et al. |
| 5,300,031 A | 4/1994 | Neer et al. |
| 5,308,330 A | 5/1994 | Grimard |
| 5,314,415 A | 5/1994 | Liebert et al. |

(56) References Cited

U.S. PATENT DOCUMENTS

| | | |
|---|---|---|
| 5,317,506 A | 5/1994 | Coutre et al. |
| 5,324,273 A | 6/1994 | Discko, Jr. |
| 5,336,189 A | 8/1994 | Sealfon |
| 5,338,309 A | 8/1994 | Imbert |
| 5,342,298 A | 8/1994 | Michaels et al. |
| 5,353,691 A | 10/1994 | Haber et al. |
| 5,354,287 A | 10/1994 | Wacks |
| 5,356,375 A | 10/1994 | Higley |
| 5,356,393 A | 10/1994 | Haber et al. |
| 5,373,684 A | 12/1994 | Vacca |
| 5,380,285 A | 1/1995 | Jenson |
| 5,383,858 A | 1/1995 | Reilly et al. |
| 5,389,075 A | 2/1995 | Vladimirsky |
| 5,397,313 A | 3/1995 | Gross |
| 5,411,488 A | 5/1995 | Pagay et al. |
| 5,413,563 A | 5/1995 | Basile et al. |
| 5,425,716 A | 6/1995 | Kawasaki et al. |
| 5,429,602 A | 7/1995 | Hauser |
| 5,429,611 A | 7/1995 | Rait |
| 5,431,627 A | 7/1995 | Pastrone et al. |
| 5,433,712 A | 7/1995 | Stiles et al. |
| 5,439,452 A | 8/1995 | McCarty |
| 5,445,622 A | 8/1995 | Brown |
| 5,451,211 A | 9/1995 | Neer et al. |
| 5,456,670 A | 10/1995 | Neer et al. |
| 5,478,314 A | 12/1995 | Malenchek |
| 5,484,413 A | 1/1996 | Gevorgian |
| 5,512,054 A | 4/1996 | Morningstar |
| 5,520,653 A | 5/1996 | Reilly et al. |
| 5,531,698 A | 7/1996 | Olsen |
| 5,531,710 A | 7/1996 | Dang et al. |
| 5,533,981 A | 7/1996 | Mandro et al. |
| 5,535,746 A | 7/1996 | Hoover et al. |
| 5,540,660 A | 7/1996 | Jenson |
| 5,545,140 A | 8/1996 | Conero et al. |
| 5,573,515 A | 11/1996 | Wilson et al. |
| 5,593,386 A | 1/1997 | Helldin |
| 5,624,408 A | 4/1997 | Helldin |
| 5,658,261 A | 8/1997 | Neer et al. |
| 5,662,612 A | 9/1997 | Niehoff |
| 5,681,285 A | 10/1997 | Ford et al. |
| 5,681,286 A | 10/1997 | Niehoff |
| 5,683,367 A | 11/1997 | Jordan et al. |
| 5,688,252 A | 11/1997 | Matsuda et al. |
| 5,695,477 A | 12/1997 | Sfikas |
| 5,722,951 A | 3/1998 | Marano |
| 5,735,825 A | 4/1998 | Stevens et al. |
| 5,738,655 A | 4/1998 | Vallelunga et al. |
| 5,738,659 A | 4/1998 | Neer et al. |
| 5,741,227 A | 4/1998 | Sealfon |
| 5,741,232 A | 4/1998 | Reilly et al. |
| 5,779,675 A | 7/1998 | Reilly et al. |
| 5,782,803 A | 7/1998 | Jentzen |
| 5,785,682 A | 7/1998 | Grabenkort |
| 5,795,333 A | 8/1998 | Reilly et al. |
| 5,807,334 A | 9/1998 | Hodosh et al. |
| 5,808,203 A | 9/1998 | Nolan, Jr. et al. |
| 5,827,219 A | 10/1998 | Uber, III et al. |
| 5,827,262 A | 10/1998 | Neftel et al. |
| 5,840,026 A | 11/1998 | Uber, III et al. |
| RE35,979 E | 12/1998 | Reilly et al. |
| 5,865,805 A | 2/1999 | Ziemba |
| 5,873,861 A | 2/1999 | Hitchins et al. |
| 5,879,336 A | 3/1999 | Brinon |
| 5,882,343 A | 3/1999 | Wilson et al. |
| 5,899,885 A | 5/1999 | Reilly et al. |
| 5,902,276 A | 5/1999 | Namey, Jr. |
| 5,913,844 A | 6/1999 | Ziemba et al. |
| 5,919,167 A | 7/1999 | Mulhauser et al. |
| 5,938,637 A | 8/1999 | Austin et al. |
| 5,938,639 A | 8/1999 | Reilly et al. |
| 5,944,694 A | 8/1999 | Hitchins et al. |
| 5,947,929 A | 9/1999 | Trull |
| 5,947,935 A | 9/1999 | Kazousky et al. |
| 5,954,697 A | 9/1999 | Srisathapat et al. |
| 5,954,700 A | 9/1999 | Kovelman |
| 5,997,502 A | 12/1999 | Reilly et al. |
| 5,997,511 A | 12/1999 | Curie et al. |
| 6,004,300 A | 12/1999 | Butcher et al. |
| 6,017,330 A | 1/2000 | Hitchins et al. |
| 6,042,565 A | 3/2000 | Hirschman et al. |
| 6,048,334 A | 4/2000 | Hirschman et al. |
| 6,059,756 A | 5/2000 | Yeh |
| 6,080,136 A | 6/2000 | Trull et al. |
| 6,083,197 A | 7/2000 | Umbaugh |
| 6,083,200 A | 7/2000 | Grimm et al. |
| 6,090,064 A | 7/2000 | Reilly et al. |
| 6,099,502 A | 8/2000 | Duchon et al. |
| 6,129,712 A | 10/2000 | Sudo et al. |
| 6,162,200 A | 12/2000 | Sawa et al. |
| 6,196,999 B1 | 3/2001 | Goethel et al. |
| 6,221,045 B1 | 4/2001 | Duchon et al. |
| 6,224,577 B1 | 5/2001 | Dedola et al. |
| 6,267,749 B1 | 7/2001 | Miklos et al. |
| 6,315,758 B1 | 11/2001 | Neer et al. |
| 6,322,535 B1 | 11/2001 | Hitchins et al. |
| RE37,487 E | 12/2001 | Reilly et al. |
| 6,336,913 B1 | 1/2002 | Spohn et al. |
| 6,339,718 B1 | 1/2002 | Zatezalo et al. |
| 6,345,262 B1 | 2/2002 | Madden |
| 6,432,089 B1 | 8/2002 | Kakimi et al. |
| 6,447,487 B1 | 9/2002 | Cane' |
| 6,511,459 B1 | 1/2003 | Fago |
| 6,517,516 B1 | 2/2003 | Caizza |
| 6,533,758 B1 | 3/2003 | Staats et al. |
| 6,582,399 B1 | 6/2003 | Smith et al. |
| 6,585,700 B1 | 7/2003 | Trocki et al. |
| 6,652,489 B2 | 11/2003 | Trocki et al. |
| 6,659,979 B2 | 12/2003 | Neer et al. |
| 6,669,663 B1 | 12/2003 | Thompson |
| 6,733,477 B2 | 5/2004 | Cowan et al. |
| 6,733,478 B2 | 5/2004 | Reilly et al. |
| 6,752,789 B2 | 6/2004 | Duchon et al. |
| 6,764,466 B1 | 7/2004 | Staats et al. |
| 6,808,513 B2 | 10/2004 | Reilly et al. |
| 6,817,990 B2 | 11/2004 | Yap et al. |
| 6,958,053 B1 | 10/2005 | Reilly |
| 7,018,363 B2 | 3/2006 | Cowan et al. |
| 7,029,459 B2 | 4/2006 | Reilly |
| 7,300,417 B1 | 11/2007 | Goethel et al. |
| 7,337,538 B2 | 3/2008 | Moutafis et al. |
| 7,399,293 B2 | 7/2008 | Oyibo et al. |
| 7,419,478 B1 | 9/2008 | Reilly et al. |
| 7,455,659 B2 | 11/2008 | Nemoto et al. |
| 7,462,166 B2 | 12/2008 | Kowan et al. |
| 7,465,290 B2 | 12/2008 | Reilly |
| 7,497,843 B1 | 3/2009 | Castillo et al. |
| 7,501,092 B2 | 3/2009 | Chen |
| 7,540,856 B2 | 6/2009 | Hitchins |
| 7,553,294 B2 | 6/2009 | Lazzaro et al. |
| 7,566,326 B2 | 7/2009 | Duchon et al. |
| 7,666,169 B2 | 2/2010 | Cowan et al. |
| 7,682,345 B2 | 3/2010 | Savage |
| 7,803,134 B2 | 9/2010 | Sharifi et al. |
| 7,972,306 B2 | 7/2011 | Shearn |
| 3,012,125 A1 | 9/2011 | Fago et al. |
| 8,012,124 B1 | 9/2011 | Fago et al. |
| 8,038,656 B2 | 10/2011 | Lloyd et al. |
| 8,070,732 B2 | 12/2011 | Rochette |
| 8,105,293 B2 | 1/2012 | Pickhard |
| 8,172,814 B2 | 5/2012 | Cane et al. |
| 8,177,757 B2 | 5/2012 | Nemoto et al. |
| 8,308,689 B2 | 11/2012 | Lewis |
| 8,353,879 B2 | 1/2013 | Goethel et al. |
| 8,475,415 B2 | 7/2013 | Schiller et al. |
| 8,480,631 B2 | 7/2013 | Wotton et al. |
| 8,585,658 B2 | 11/2013 | Forstreuter |
| 8,613,730 B2 | 12/2013 | Hieb et al. |
| 8,628,495 B2 | 1/2014 | Horton et al. |
| 8,721,596 B2 | 5/2014 | Trocki et al. |
| 8,740,854 B2 | 6/2014 | Schiller et al. |
| 8,740,856 B2 | 6/2014 | Quinn et al. |
| 8,845,596 B2 | 9/2014 | Berman et al. |
| 8,851,866 B2 | 10/2014 | Moutafis et al. |

(56) References Cited

U.S. PATENT DOCUMENTS

| | | |
|---|---|---|
| 8,857,674 B2 | 10/2014 | Nighy et al. |
| 8,864,712 B1 | 10/2014 | Fago et al. |
| 8,926,569 B2 | 1/2015 | Bisegna et al. |
| 8,932,255 B1 | 1/2015 | Fago et al. |
| 8,945,051 B2 | 2/2015 | Schriver et al. |
| 9,173,995 B1 | 11/2015 | Tucker et al. |
| 9,174,003 B2 | 11/2015 | Cowan et al. |
| 9,199,033 B1 | 12/2015 | Cowan et al. |
| 9,474,857 B2 | 10/2016 | Riley et al. |
| 9,636,452 B2 | 5/2017 | Trocki et al. |
| 9,694,131 B2 | 7/2017 | Cowan et al. |
| 9,844,622 B2 | 12/2017 | Savage et al. |
| 2003/0004468 A1 | 1/2003 | Righi et al. |
| 2003/0009133 A1 | 1/2003 | Ramey |
| 2003/0120219 A1 | 6/2003 | Nielsen et al. |
| 2003/0153877 A1 | 8/2003 | Huang et al. |
| 2003/0163089 A1 | 8/2003 | Bynum |
| 2003/0216683 A1 | 11/2003 | Shekalim |
| 2003/0236800 A1 | 12/2003 | Goeltzenleuchter et al. |
| 2004/0006314 A1 | 1/2004 | Campbell et al. |
| 2004/0039368 A1 | 2/2004 | Reilly et al. |
| 2004/0074453 A1 | 4/2004 | Roelle et al. |
| 2004/0116861 A1 | 6/2004 | Trocki et al. |
| 2004/0133153 A1 | 7/2004 | Trocki et al. |
| 2004/0133183 A1 | 7/2004 | Trocki et al. |
| 2004/0186437 A1 | 9/2004 | Frenette et al. |
| 2004/0243022 A1 | 12/2004 | Carney et al. |
| 2004/0243067 A1 | 12/2004 | Sibbitt |
| 2005/0113754 A1 | 5/2005 | Cowan |
| 2005/0240149 A1 | 10/2005 | Lu |
| 2006/0129104 A1 | 6/2006 | Cowan et al. |
| 2006/0173411 A1 | 8/2006 | Barere |
| 2007/0123830 A1 | 5/2007 | Johannes et al. |
| 2007/0191785 A1 | 8/2007 | Barere et al. |
| 2009/0247957 A1 | 10/2009 | Heutschi |
| 2009/0326459 A1 | 12/2009 | Shipway et al. |
| 2010/0016796 A1 | 1/2010 | Derichs |
| 2010/0130961 A1 | 5/2010 | Tucker |
| 2010/0318030 A1 | 12/2010 | Jenkins |
| 2011/0178500 A1 | 7/2011 | Shang et al. |
| 2011/0224611 A1 | 9/2011 | Lum et al. |
| 2012/0039809 A1 | 2/2012 | Levinson et al. |
| 2012/0184920 A1 | 7/2012 | Okihara et al. |
| 2013/0211325 A1 | 8/2013 | Wang et al. |
| 2013/0317427 A1 | 11/2013 | Brereton et al. |
| 2013/0317480 A1 | 11/2013 | Reber et al. |
| 2013/0338605 A1 | 12/2013 | Chen |
| 2014/0031763 A1 | 1/2014 | Soma et al. |
| 2014/0200483 A1 | 7/2014 | Fojtik |
| 2014/0330216 A1 | 11/2014 | Weaver et al. |
| 2017/0043082 A1 | 2/2017 | Cowan et al. |
| 2020/0289765 A1 | 9/2020 | Bisegna |

FOREIGN PATENT DOCUMENTS

| | | |
|---|---|---|
| DE | 3227417 A1 | 2/1983 |
| DE | 4017920 A1 | 12/1991 |
| DE | 19601214 A1 | 8/1996 |
| DE | 19633530 A1 | 2/1998 |
| EP | 0111724 A2 | 6/1984 |
| EP | 0160303 A2 | 11/1985 |
| EP | 0164904 A2 | 12/1985 |
| EP | 0308380 A2 | 3/1989 |
| EP | 0319275 A1 | 6/1989 |
| EP | 0320168 A1 | 6/1989 |
| EP | 0323321 A1 | 7/1989 |
| EP | 0346950 A2 | 12/1989 |
| EP | 0364010 A2 | 4/1990 |
| EP | 0384657 A1 | 8/1990 |
| EP | 0482677 A1 | 4/1992 |
| EP | 0523343 A1 | 1/1993 |
| EP | 0523434 A1 | 1/1993 |
| EP | 0567944 A1 | 11/1993 |
| EP | 0567945 A1 | 11/1993 |
| EP | 0584531 A2 | 3/1994 |
| EP | 0736306 A1 | 10/1996 |
| EP | 0749757 A2 | 12/1996 |
| EP | 0900573 A2 | 3/1999 |
| EP | 0919251 A2 | 6/1999 |
| EP | 0951306 A2 | 10/1999 |
| EP | 1002551 A2 | 5/2000 |
| EP | 1166807 A1 | 1/2002 |
| GB | 847914 A | 9/1960 |
| GB | 1380873 A | 1/1975 |
| GB | 2108852 A | 5/1983 |
| JP | S61500415 A | 3/1986 |
| JP | S6327770 A | 2/1988 |
| JP | S6368177 A | 3/1988 |
| JP | 2001029466 A | 2/2001 |
| JP | 4462798 B2 | 5/2010 |
| JP | D1398129 | 10/2010 |
| JP | D1398130 | 10/2010 |
| JP | D1400385 | 11/2010 |
| JP | D1400386 | 11/2010 |
| JP | D1400551 | 11/2010 |
| JP | D1400552 | 11/2010 |
| JP | 2012143381 A | 8/2012 |
| WO | 8002376 A1 | 11/1980 |
| WO | 8500292 A1 | 1/1985 |
| WO | 8502256 A1 | 5/1985 |
| WO | 8906145 A1 | 7/1989 |
| WO | 8909071 A1 | 10/1989 |
| WO | 8911310 A1 | 11/1989 |
| WO | 9001962 A1 | 3/1990 |
| WO | 9104759 A1 | 4/1991 |
| WO | 9221391 A1 | 12/1992 |
| WO | 9413336 A1 | 6/1994 |
| WO | 9425089 A1 | 11/1994 |
| WO | 9632975 A1 | 10/1996 |
| WO | 9707841 A2 | 3/1997 |
| WO | 9736635 A1 | 10/1997 |
| WO | 9820920 A2 | 5/1998 |
| WO | 9965548 A1 | 12/1999 |
| WO | 0137903 A2 | 5/2001 |
| WO | 0137905 A2 | 5/2001 |
| WO | 0204049 A1 | 1/2002 |
| WO | 03101527 A1 | 12/2003 |
| WO | 2004035289 A1 | 4/2004 |
| WO | 2005053771 A2 | 6/2005 |
| WO | 2007130061 A1 | 11/2007 |
| WO | 2010139793 A1 | 12/2010 |
| WO | 2012124028 A1 | 9/2012 |
| WO | 2012155035 A1 | 11/2012 |
| WO | 2015006430 A1 | 1/2015 |
| WO | 2015106107 A1 | 7/2015 |
| WO | 2016112163 A1 | 7/2016 |
| WO | 2018129116 A1 | 7/2018 |

OTHER PUBLICATIONS

Brochure for "Angiomat CT" of Liebel-Farsheim, 2111 E. Galbraith Road, Cincinnati, OH 45215, @ 1988.

Brochure for "Cordis Lymphography Injector," Cordis Corporation, Miami, FL 33137 (1972).

Brochure for "PercuPump 1A" of E-Z-Em, Inc, 717 Main Street, Westbury, NY 11590, @ 1990.

Brochure for the "The First and Only True Injection System, " Medrad Mark V System, Control No. 85106-00-BA-02, Nov. 1988.

Injektron 82 MRT User Instructions, Version MR2, CEO535, MedTron GmbH(Mar. 10, 1999).

"International Preliminary Report on Patentability of PCT Application No. PCT/US2019/019360", dated Sep. 3, 2020.

Liebel-Flarsheim company—Angiomat 6000 Digital Injection System Operator's Manual, 600950 Rev 1 (1990); p. 3-6 to 3-8, 4-52 to 4-56.

Medrad Envision CT Injector Operation Manual, EOM 700E, 92401-T-123 Rev E, Copyright 1995.

Medrad Envision CT Injector Operation Manual, EOM 700E, 92401-T-123 Rev E, pp. 2-10 to 2-11 and pp. 2-30 to 2-35(Copyright 1995).

Medrad, Mark V/Mark V Plus Injector Operation Manual, KMP 805P Rev. B (1990); pp. 1-18 to 1-28, 3-7 to 3-13, 14-1 to 14-4.

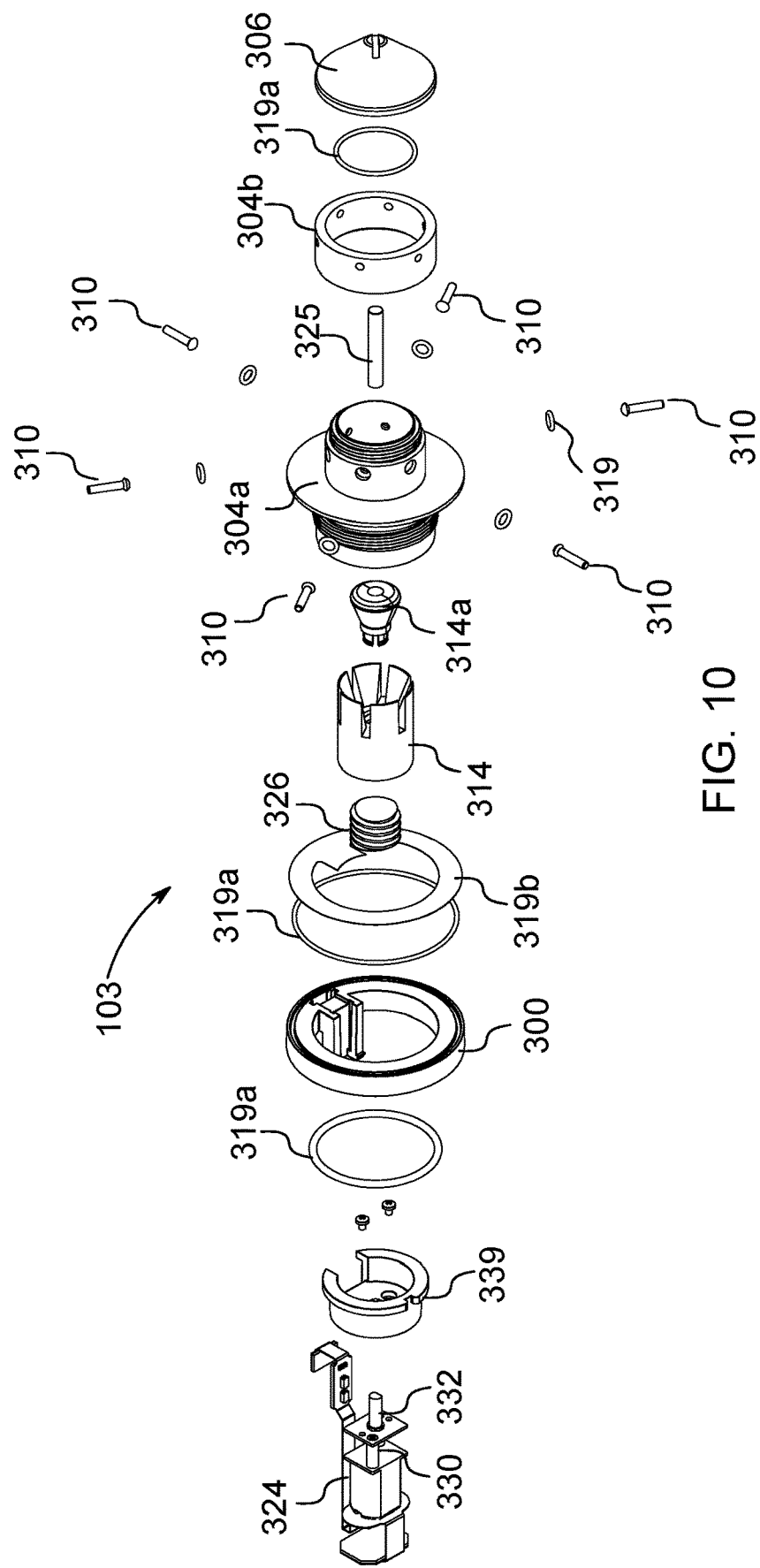

SYRINGE PLUNGER ENGAGEMENT MECHANISM

CROSS-REFERENCE TO RELATED APPLICATIONS

The present application is a U.S. national phase application under 35 U.S.C. § 371 of PCT International Application No. PCT/US2019/019360, filed 25 Feb. 2019 and claims priority to U.S. Provisional Application No. 62/635,669, filed 27 Feb. 2018, the disclosures of which are incorporated herein in their entirety.

BACKGROUND OF THE DISCLOSURE

Field of the Disclosure

The present disclosure is related to syringes and medical injectors for use in the medical field and, more particularly, to syringes having a reciprocally slidable plunger disposed within a syringe barrel, the plunger having an engagement portion configured for releasably engaging with a syringe plunger engagement mechanism on a piston of a powered fluid injector. The present disclosure further relates to powered fluid injectors having the syringe plunger engagement mechanism for engaging the engagement portion of a plunger of the at least one syringe.

Description of the Related Art

In many medical diagnostic and therapeutic procedures, a medical practitioner, such as a physician, injects a patient with one or more medical fluids. In recent years, a number of medical fluid delivery systems for pressurized injection of fluids, such as a contrast solution (often referred to simply as "contrast"), a flushing agent, such as saline, and other medical fluids, have been developed for use in procedures such as angiography, computed tomography (CT), ultrasound, magnetic resonance imaging (MRI), positron emission tomography (PET), and other molecular imaging procedures. In general, these medical fluid delivery systems, such as powered fluid injectors, are designed to deliver a preset amount of fluid at a preset flow rate.

Typically, powered fluid injectors have one or more pistons that releasably connect to a plunger of one or more syringes. The plunger is slidably disposed within the barrel such that the piston can drive the plunger in a proximal and/or distal direction relative to a longitudinal axis of the barrel to draw fluid into the syringe barrel or deliver the fluid from the syringe barrel.

While various syringe plunger engagement mechanisms for releasably connecting the piston to the plunger are known in the medical field, improved engagement mechanisms continue to be in demand. In particular, there exists a need for powered fluid injectors having a syringe plunger engagement mechanism that facilitates a reliable and robust connection and corresponding disconnection with the syringe plunger to enable reciprocal movement of the plunger within the syringe barrel via reciprocal movement of the piston.

SUMMARY OF DISCLOSURE

The present disclosure generally relates to syringes having a reciprocally slidable plunger disposed within a syringe barrel, where the plunger has an engagement portion configured for releasably engaging/disengaging with a plunger engagement mechanism on at least one piston of a powered fluid injector. The present disclosure further relates to powered fluid injectors having at least one piston, where the at least one piston has a plunger engagement mechanism for selectively engaging/disengaging the engagement portion of the plunger.

In some examples of the present disclosure, the fluid injector system may have at least one reciprocally operable piston having a piston head, and a plunger engagement mechanism associated with the piston head. The plunger engagement mechanism may include a cam sleeve disposed within the piston head and movable relative to the piston head, the cam sleeve having one or more tracks defining a cam surface. The plunger engagement mechanism may further have an actuator operatively connected to the cam sleeve for moving the cam sleeve relative to the piston head, and one or more pins disposed within the cam sleeve. The one or more pins may be reversibly movable within the one or more tracks with reversible movement of the cam sleeve between a first, withdrawn or disengaged position, wherein the one or more pins are radially withdrawn into the piston head and a second, extended or engaged position, wherein the one or more pins protrude radially outward relative to an outer surface of the piston head, where the one or more pins are configured to engage a pin engagement surface, such as a radially inward facing ledge, on an interior portion of the plunger when the one or more pins are in the second position.

In other examples of the present disclosure, the piston head may have one or more openings through which the one or more pins are reversibly movable between the first position and the second position. The one or more pins may be configured to engage or disengage a pin engagement surface on a plunger when the one or more pins are in the second or extended position or moved to the first, retracted position, respectively. The cam sleeve may be reversibly movable axially in a direction along a longitudinal axis of the piston head. The cam sleeve may have a threaded interface for threadably interacting with a screw operatively connected with the actuator. The threaded interface may have a female thread or a male thread, and wherein the screw has a corresponding male thread or a female thread. The screw may be connected with the actuator via an output shaft. The actuator may be a rotary electric motor, a linear electric motor, a linear actuator, or a solenoid. Rotational movement of the actuator may reversibly move the cam sleeve in a linear direction. Linear movement of the actuator may move the cam sleeve in an axial direction along a longitudinal axis of the piston head. The actuator may be operatively connected to a controller for controlling rotary motion of the actuator, including the rotary direction of the actuator.

According to another embodiment, the present disclosure provides a piston for a fluid injector. The piston may comprise a piston head and a plunger engagement mechanism associated with the piston head. The plunger engagement mechanism may include a cam sleeve disposed within the piston head and movable relative to the piston head, the cam sleeve having one or more tracks defining a cam surface. The plunger engagement mechanism may further have an actuator operatively connected to the cam sleeve for moving the cam sleeve relative to the piston head, and one or more pins at least partially disposed within the cam sleeve. The one or more pins may be reversibly movable within the one or more tracks with reversible movement of the cam sleeve between a first, withdrawn or disengaged position, wherein the one or more pins are radially withdrawn into the piston head and a second, extended or engaged position, wherein the one or more pins protrude radially outward relative to an outer surface of the piston head, where the one or more pins are configured to engage a pin engagement surface, such as a radially inward facing ledge, on an interior portion of the plunger when the one or more pins are in the second position.

Other examples of the present disclosure generally relate to a method for engaging a syringe plunger with a piston head of a fluid injector system. The method may include advancing the piston head at least partially into an interior cavity of the plunger, and advancing a cam sleeve disposed in the piston head in an axial direction relative to the piston head. Advancement of the cam sleeve may cause one or more pins at least partially disposed in one or more tracks of the cam sleeve to move from a first or withdrawn position, where the one or more pins are radially withdrawn into the piston head, to a second or extended position, where the one or more pins protrude radially outward to engage at least a portion of the plunger.

Other examples of the present disclosure generally relate to a plunger engagement mechanism for a piston head of a fluid injector system. The plunger engagement mechanism may include a cam sleeve movable relative to the piston head. The cam sleeve may have one or more tracks defining a cam surface. The plunger engagement mechanism may further include an actuator operatively connected to the cam sleeve for moving the cam sleeve relative to the piston head, and one or more pins at least partially disposed in and moveable within the one or more tracks of the cam sleeve. Movement of the cam sleeve may cause movement of the one or pins within the one or more tracks. The one or more pins may be moveable between a first or withdrawn position, where the one or more pins are radially withdrawn into the piston head, and a second or extended position, where the one or more pins protrude radially outward relative to an outer surface of the piston head.

In accordance with other examples, the disclosure of the present application may be characterized by one or more of the following clauses:

Clause 1. A fluid injector system comprising: at least one reciprocally operable piston having a piston head; and a plunger engagement mechanism associated with the piston head, the plunger engagement mechanism comprising: a cam sleeve disposed within the piston head and movable relative to the piston head, the cam sleeve having one or more tracks defining a cam surface; an actuator operatively connected to the cam sleeve for reversibly moving the cam sleeve relative to the piston head; and one or more pins disposed within the cam sleeve and movable within the one or more tracks with movement of the cam sleeve between a first, disengaged position, wherein the one or more pins are radially withdrawn into the piston head and a second, engaged position, wherein the one or more pins protrude radially outward relative to an outer surface of the piston head.

Clause 2. The fluid injector system of clause 1, wherein the piston head comprises one or more openings through which the one or more pins are movable between the first, disengaged position and the second, engaged position.

Clause 3. The fluid injector system of clause 1 or 2, wherein the one or more pins are configured to engage a pin engagement surface on a portion of a plunger when the one or more pins are in the second, engaged position.

Clause 4. The fluid injector system of any of clauses 1 to 3, wherein the cam sleeve is movable axially in a direction along a longitudinal axis of the piston head.

Clause 5. The fluid injector system of any of clauses 1 to 4, wherein the cam sleeve has a threaded interface for threadably interacting with a screw operatively connected with the actuator.

Clause 6. The fluid injector system of clause 5, wherein the threaded interface has a female thread or a male thread, and wherein the screw has a corresponding male thread or a female thread.

Clause 7. The fluid injector system of any of clauses 5 to 6, wherein the screw is connected with the actuator via an output shaft.

Clause 8. The fluid injector system of any of clauses 1 to 7, wherein each of the one or more tracks diverge from a longitudinal axis of the plunger head in a proximal to distal direction, such that a distal end of the track is radially farther from the longitudinal axis than a proximal end of the track.

Clause 9. The fluid injector system of any of clauses 1 to 8, wherein each of the one or more pins has a bulbous end received in one or the one or more tracks.

Clause 10. The fluid injector system of any of claims 1 to 9, wherein each of the one or more tracks has a diagonally linear shape or an arcuate shape.

Clause 11. The fluid injector system of any of clauses 1 to 10, wherein the actuator is at least one of a rotary electric motor, a linear electric motor, a linear actuator, and a solenoid.

Clause 12. The fluid injector system of any of clauses 1 to 11, wherein rotational movement of the actuator reversibly moves the cam sleeve axially in a direction along a longitudinal axis of the piston head.

Clause 13. The fluid injector system of any of clauses 1 to 11, wherein linear movement of the actuator moves the cam sleeve axially in a direction along a longitudinal axis of the piston head.

Clause 14. The fluid injector system of any of clauses 1 to 12, wherein the actuator is operatively connected to a controller for controlling rotary motion of the actuator.

Clause 15. A piston for a fluid injector, the piston comprising: a piston head; and a plunger engagement mechanism associated with the piston head, the plunger engagement mechanism comprising: a cam sleeve disposed within the piston head and movable relative to the piston head, the cam sleeve having one or more tracks defining a cam surface; an actuator operatively connected to the cam sleeve for moving the cam sleeve relative to the piston head; and one or more pins disposed within the cam sleeve and movable within the one or more tracks with movement of the cam sleeve between a first, disengaged position, wherein the one or more pins are radially withdrawn into the piston head and a second, engaged position, wherein the one or more pins protrude radially outward relative to an outer surface of the piston head.

Clause 16. The piston of clause 15, wherein the piston head comprises one or more openings through which the one or more pins are movable between the first, disengaged position and the second, engaged position.

Clause 17. The piston of clause 15 or 16, wherein the one or more pins are configured to engage a pin engagement surface on a portion of a plunger when the one or more pins are in the second, engaged position.

Clause 18. The piston of any of clauses 15 to 17, wherein the cam sleeve is movable axially in a direction along a longitudinal axis of the piston head.

Clause 19. The piston of any of clauses 15 to 18, wherein the cam sleeve has a threaded interface for threadably interacting with a screw operatively connected with the actuator.

Clause 20. The piston of clause 19, wherein the threaded interface has a female thread or a male thread, and wherein the screw has a corresponding male thread or a female thread.

Clause 21. The piston of clause 19 or 20, wherein the screw is connected with the actuator via an output shaft.

Clause 22. The piston of any of clauses 15 to 21, wherein the actuator is a rotary electric motor, a linear electric motor, a linear actuator, or a solenoid.

Clause 23. The piston of any of clauses 15 to 22, wherein rotational movement of the actuator reversibly moves the cam sleeve axially in a direction along a longitudinal axis of the piston head.

Clause 24. The piston of any of clauses 15 to 22, wherein linear movement of the actuator moves the cam sleeve in movable axially in a direction along a longitudinal axis of the piston head.

Clause 25. The piston of any of clauses 15 to 23, wherein the actuator is operatively connected to a controller for controlling a rotary motion of the actuator.

Clause 26. A method for engaging a syringe plunger with a piston head of a fluid injector system, the method comprising: advancing the piston head at least partially into an interior cavity of the plunger; and advancing a cam sleeve disposed in the piston head in an axial direction relative to the piston head, wherein advancement of the cam sleeve causes one or more pins at least partially disposed in one or more tracks of the cam sleeve to move from a first, disengaged position, wherein the one or more pins are radially withdrawn into the piston head, to a second, engaged position, wherein the one or more pins protrude radially outward to engage at least a portion of the syringe plunger.

Clause 27. The method of clause 26, wherein advancing the cam sleeve relative to the piston head comprises rotating a screw operatively connected with a threaded interface of the cam sleeve.

Clause 28. The method of clause 27, wherein the screw is rotated by a rotary electric motor.

Clause 29. The method of any of clauses 26 to 28, wherein advancing the cam sleeve relative to the piston head comprises moving the cam sleeve towards a distal end of the piston head.

Clause 30. The method of any of clauses 26 to 29, wherein the one or more pins engage a pin engagement surface on a portion of the syringe plunger when the one or more pins are in the second, engaged position.

Clause 31. A plunger engagement mechanism for a piston head of a fluid injector system, the plunger engagement mechanism comprising: a cam sleeve movable relative to the piston head, the cam sleeve having one or more tracks defining a cam surface, an actuator operatively connected to the cam sleeve for moving the cam sleeve relative to the piston head; and one or more pins at least partially disposed in and moveable within the one or more tracks of the cam sleeve, wherein movement of the cam sleeve causes movement of the one or pins within the one or more tracks, the one or more pins moveable between a first, disengaged position, wherein the one or more pins are radially withdrawn into the piston head, and a second, engaged position, wherein the one or more pins protrude radially outward relative to an outer surface of the piston head.

Clause 32. The plunger engagement mechanism of clause 31, wherein the piston head comprises one or more openings through which the one or more pins are movable between the first, disengaged position and the second, engaged position.

Clause 33. The plunger engagement mechanism of clause 31 or 32, wherein the one or more pins are configured to engage a pin engagement surface on a portion of a plunger when the one or more pins are in the second, engaged position.

Clause 34. The plunger engagement mechanism of any of clauses 31 to 33, wherein the cam sleeve is movable axially in a direction along a longitudinal axis of the piston head.

Clause 35. The plunger engagement mechanism of any of clauses 31 to 34, wherein the cam sleeve has a threaded interface for threadably interacting with a screw operatively connected with the actuator.

Clause 36. The plunger engagement mechanism of clause 35, wherein the threaded interface has a female thread or a male thread, and wherein the screw has a corresponding male thread or a female thread.

Clause 37. The plunger engagement mechanism of clause 36, wherein the screw is connected with the actuator via an output shaft.

Clause 38. The plunger engagement mechanism of any of clauses 31 to 36, wherein each of the one or more tracks diverge from a longitudinal axis of the plunger head in a proximal to distal direction, such that a distal end of the track is radially farther from the longitudinal axis than a proximal end of the track.

Clause 39. The plunger engagement mechanism of any of clauses 31 to 37, wherein each of the one or more pins has a bulbous end received in one or the one or more tracks.

Clause 40. The plunger engagement mechanism of any of clauses 31 to 38, wherein each of the one or more tracks has a diagonally linear shape or an arcuate shape.

Clause 41. The plunger engagement mechanism of any of clauses 31 to 40, wherein the actuator is a rotary electric motor, a linear electric motor, a linear actuator, or a solenoid.

Clause 42. The plunger engagement mechanism of any of clauses 31 to 41, wherein rotational movement of the actuator moves the cam sleeve in a linear direction.

Clause 43. The plunger engagement mechanism of any of clauses 31 to 41, wherein linear movement of the actuator moves the cam sleeve in a linear direction.

Clause 44. The plunger engagement mechanism of any of clauses 31 to 42, wherein the actuator is operatively connected to a controller for controlling rotary motion of the actuator.

These and other features and characteristics of syringe plunger engagement mechanisms, as well as the methods of operation and functions of the related elements of structures and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only.

BRIEF DESCRIPTION OF THE DRAWINGS

FIG. 10 is an exploded view of a piston of a multi-fluid delivery system in accordance with another example of the present disclosure.

DETAILED DESCRIPTION

Figure 1A:
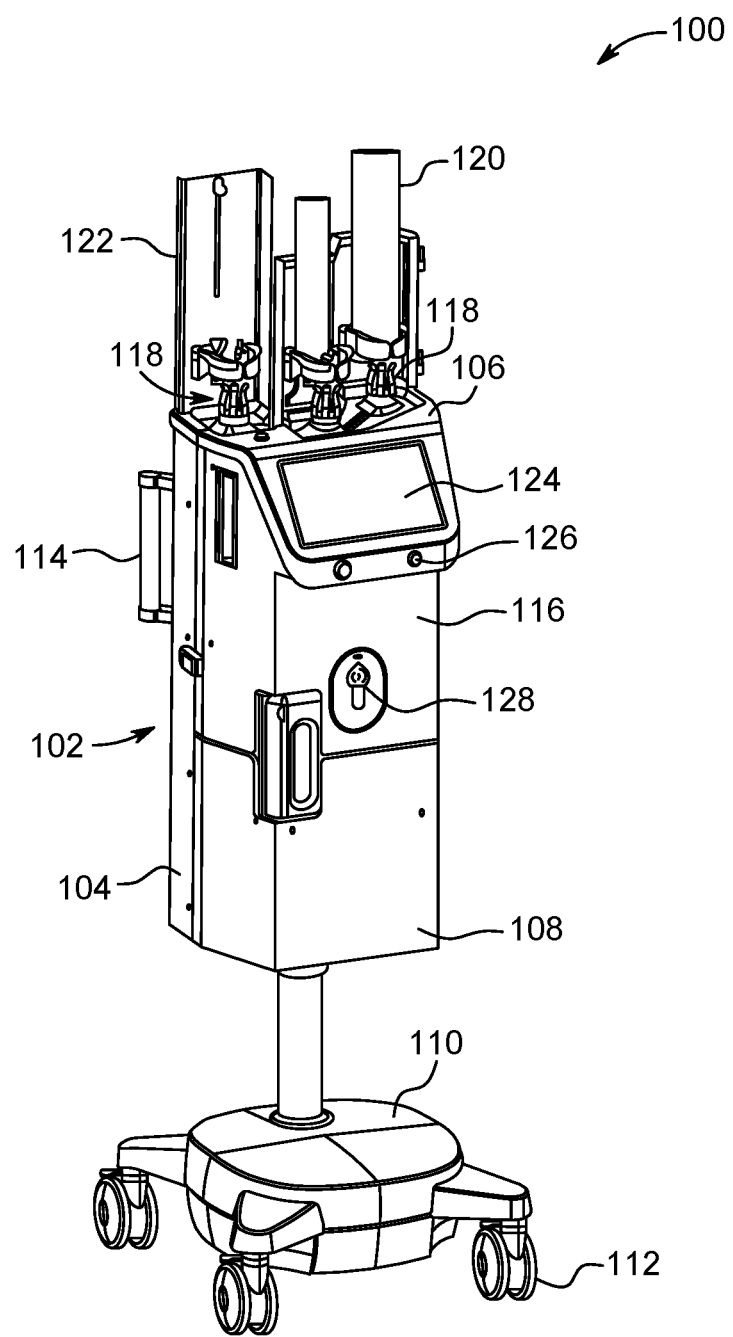
FIG. 1A is a perspective view of a multi-fluid delivery system in accordance with one example of the present disclosure.

The illustrations generally show preferred and non-limiting aspects of the systems and methods of the present disclosure. While the description presents various aspects of the devices, it should not be interpreted in any way as limiting the disclosure. Furthermore, modifications, concepts, and applications of the disclosure's aspects are to be interpreted by those skilled in the art as being encompassed, but not limited to, the illustrations and descriptions herein.

The following description is provided to enable those skilled in the art to make and use the described aspects contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation to a syringe of a multi-patient disposable set, the term "proximal" refers to a portion of a syringe nearest a piston for delivering fluid from a syringe. When used in relation to a syringe of a multi-patient disposable set, the term "distal" refers to a portion of a syringe nearest to a delivery nozzle. When used in relation to a syringe of a multi-patient disposable set, the term "radial" refers to a direction in a cross-sectional plane normal to a longitudinal axis of a syringe extending between proximal and distal ends. When used in relation to a syringe of a multi-patient disposable set, the term "circumferential" refers to a direction around an inner or outer surface of a sidewall of a syringe. When used in relation to a syringe of a multi-patient disposable set, the term "axial" refers to a direction along a longitudinal axis of a syringe extending between the proximal and distal ends. As used herein, the term "at least one of" is synonymous with "one or more of".

It is also to be understood that the specific devices and processes illustrated in the attached drawings, and described in the following specification, are simply exemplary aspects of the disclosure. Hence, specific dimensions and other physical characteristics related to the examples disclosed herein are not to be considered as limiting.

Referring to the drawings in which like reference characters refer to like parts throughout the several views thereof, the present disclosure is generally directed to a multi-fluid medical injector/injection system 100 (hereinafter "fluid injector system 100") having a multi-patient disposable set (MUDS) 130 configured for delivering fluid to a patient using a single-use disposable set (SUDS) connector. Examples of suitable MUDS 130 and SUDS configurations for embodiments of the fluid injector system 100 of the present disclosure are described in International PCT Application Publications WO 2016/112163 and WO 2105/106, 107, the disclosures of each of which is incorporated herein in its entirety by this reference. The fluid injector system 100 includes multiple components as individually described herein. Generally, the fluid injector system 100 has a powered injector administrator or device and a fluid delivery set intended to be associated with the injector to deliver one or more fluids from one or more multi-dose containers under pressure into a patient, as described herein. The various devices, components, and features of the fluid injector system 100 and the fluid delivery set associated therewith are likewise described in detail herein.

With reference to FIG. 1A, the fluid injector system 100 includes an injector housing 102 having opposed lateral sides 104, a distal or upper end 106, and a proximal or lower end 108. In some examples, the housing 102 may be supported on a base 110 having one or more wheels 112 for rotatable and movable support of the housing 102 on a floor surface. The one or more wheels 112 may be lockable to prevent the housing 102 from inadvertently moving once positioned at a desired location. At least one handle 114 may be provided to facilitate moving and positioning the fluid injector system 100. In other examples, the housing 102 may be removably or non-removably secured to a fixed surface, such as a floor, ceiling, wall, or other structure. The housing 102 encloses the various mechanical drive components, electrical and power components necessary to drive the mechanical drive components, and control components, such as electronic memory and electronic control devices (hereinafter electronic control device(s)), used to control operation of reciprocally movable pistons 103 (shown on FIG. 2) associated with the fluid injector system 100 described herein. Such pistons 103 may be reciprocally operable via electro-mechanical drive components such as a ball screw shaft driven by a motor, a voice coil actuator, a rack-and-pinion gear drive, a linear motor, and the like. In some examples, at least some of the mechanical drive components, electrical and power components, and control components may be provided on the base 110.

With reference to FIG. B, and with continued reference to FIG. 1A, the fluid injector system 100 has at least one door 116 that encloses at least some of the mechanical drive components, electrical and power components, and control components. The door 116 is desirably movable between an open position (shown in FIG. 1B) and a closed position (shown in FIG. 1A). In some examples, the door 116 may be lockable.

The fluid injector system 100 further includes at least one bulk fluid connector 118 for connection with at least one bulk fluid source 120. In some examples, a plurality of bulk fluid connectors 118 may be provided. For example, as shown in FIGS. 1A and B, three bulk fluid connectors 118 may be provided in a side-by-side or other arrangement. In some examples, the at least one bulk fluid connector 118 may be a spike configured for removably connecting to the at least one bulk fluid source 120, such as a vial, bottle, or a bag. The at least one bulk fluid connector 118 may have a reusable or non-reusable interface with each new bulk fluid source 120. The at least one bulk fluid connector 118 may be formed on or attached by tubing with the multi-patient disposable set, as described herein. The at least one bulk fluid source 120 may be configured for receiving a medical fluid, such as saline, an imaging contrast solution, or other medical fluid, for delivery to the fluid injector system 100. The housing 102 may have at least one support member 122 for supporting the at least one bulk fluid source 120 once it is connected to the fluid injector system 100.

With reference to FIG. 1A, the fluid injector system 100 includes one or more user interfaces 124, such as a graphical user interface (GUI) display window. The user interface 124 may display information pertinent to a fluid injection procedure involving the fluid injector system 100, such as current flow rate, fluid pressure, and volume remaining in the at least one bulk fluid source 120 connected to the fluid injector system 100 and may be a touch screen GUI that allows an operator to input commands and/or data for operation of the fluid injector system 100. While the user interface 124 is shown on the injector housing 102, along with control and mechanical elements of the fluid injector system 100, in some examples, the user interface 124 may be a tablet that is detachably connected to the housing 102 and is in wired or wirelessly linked communication with the housing 102. Additionally, the fluid injector system 100 and/or user interface 124 may include at least one control button 126 for tactile operation by an attendant operator of the fluid injector system 100. In certain examples, the at least one control button 126 may be part of a keyboard for inputting commands and/or data by the operator. The at least one control button 126 may be hard-wired to the electronic control device(s) associated with the fluid injector system 100 to provide direct input to the electronic control device(s). The at least one control button 126 may also be graphically part of the user interface 124, such as a touch screen. In either arrangement, the at least one control button 126 desirably provides certain individual control features to the attendant operator of the fluid injector system 100, such as but not limited to: (1) acknowledging that a multi-patient disposable set has been loaded or unloaded; (2) locking/unlocking of the multi-patient disposable set; (3) initiating and/or confirming filling/purging of the fluid injector system 100; inputting information and/or data related to the patient and/or injection procedure, and (4) initiating/stopping an injection procedure. The user interface 124 and/or any electronic processing units associated with the fluid injector system 100 may be wired or wirelessly connected to an operation and/or data storage system such as a hospital network system.

Figure 1B:
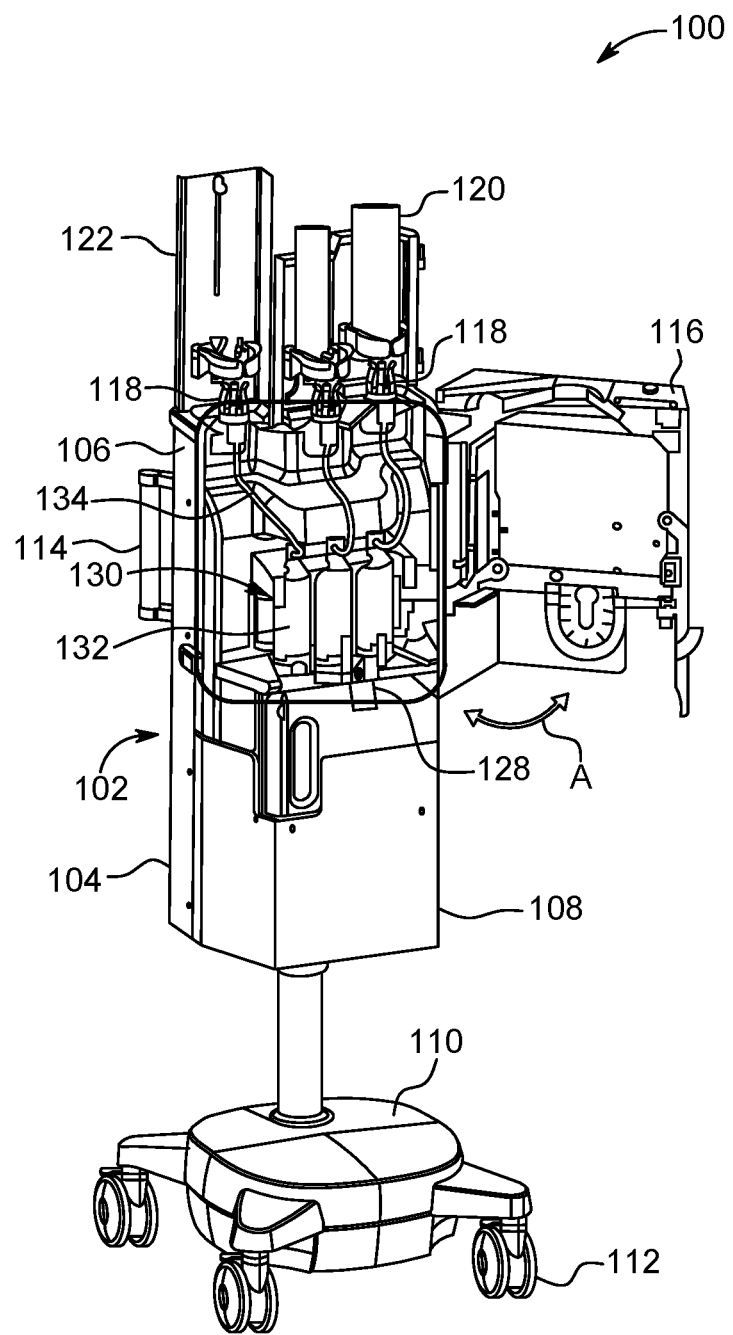
FIG. 1B is a perspective view of the multi-fluid delivery system of FIG. 1A with an access panel in an open position.

With reference to FIG. 1B, the fluid injector system includes a MUDS 130 that is removably connected to the fluid injector system 100 for delivering one or more fluids from the one or more bulk fluid sources 120 to the patient. The fluid injector system 100 includes at least one slot or access port 128 (shown in FIG. 1A) for releasably connecting a single-use disposable set to the MUDS 130, as described herein. The MUDS 130 may include one or more syringes or pumps 132. In some examples, the number of syringes 132 may correspond to the number of bulk fluid sources 120. For example, with reference to FIG. 1B, in certain embodiment the MUDS 130 has three syringes 132 in a side-by-side arrangement such that each syringe 132 is fluidly connectable to one of the bulk fluid sources 120. In some examples, one or two bulk fluid sources 120 may be connected to one or more syringes 132 of the MUDS 130. Each syringe 132 may be fluidly connectable to one of the bulk fluid sources 120 by a corresponding bulk fluid connector 118 and an associated MUDS fluid path 134. The MUDS fluid path 134 may have a spike element that connects to the bulk fluid connector 118. In some examples, the bulk fluid connector 118 may be provided directly on the MUDS 130.

Figure 2:
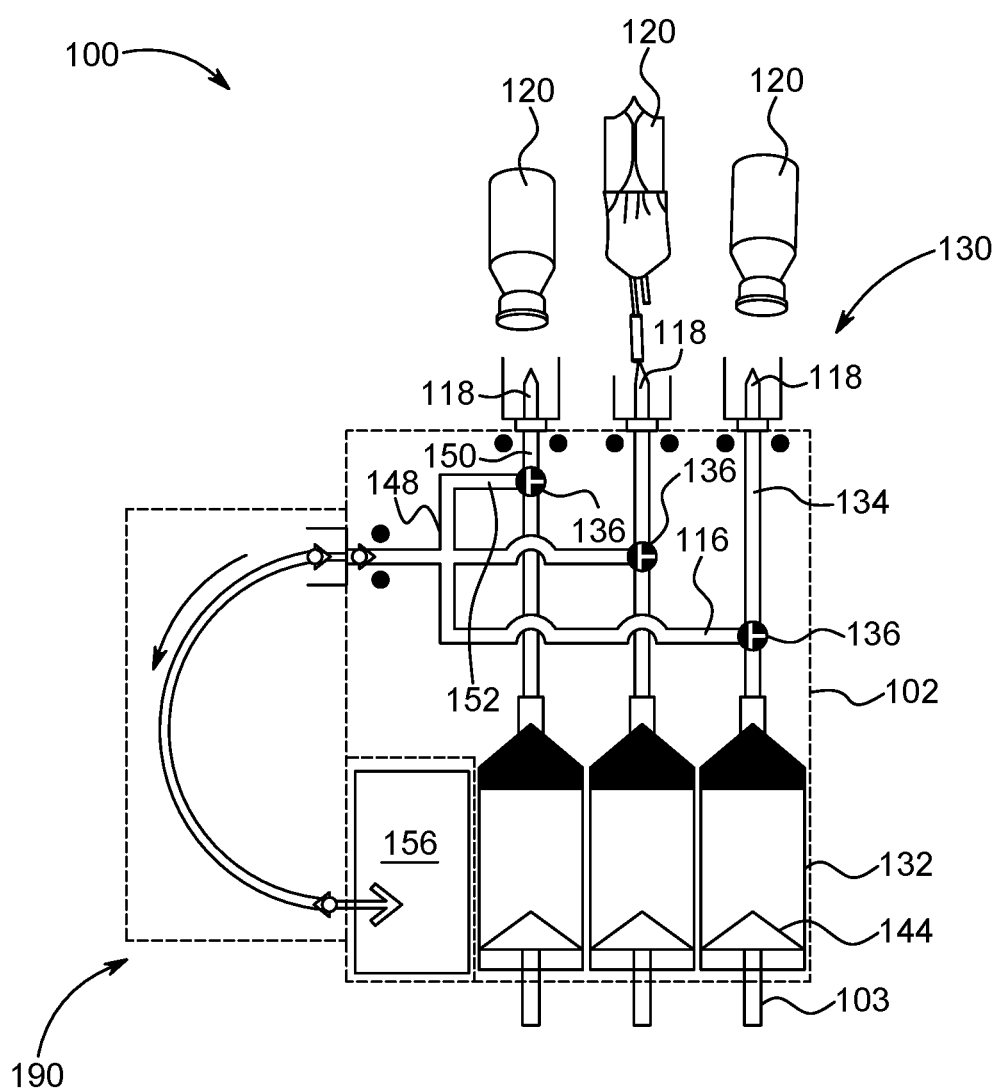
FIG. 2 is schematic view of various fluid paths within the multi-fluid delivery system of FIG. 1A.
Figure 3A:
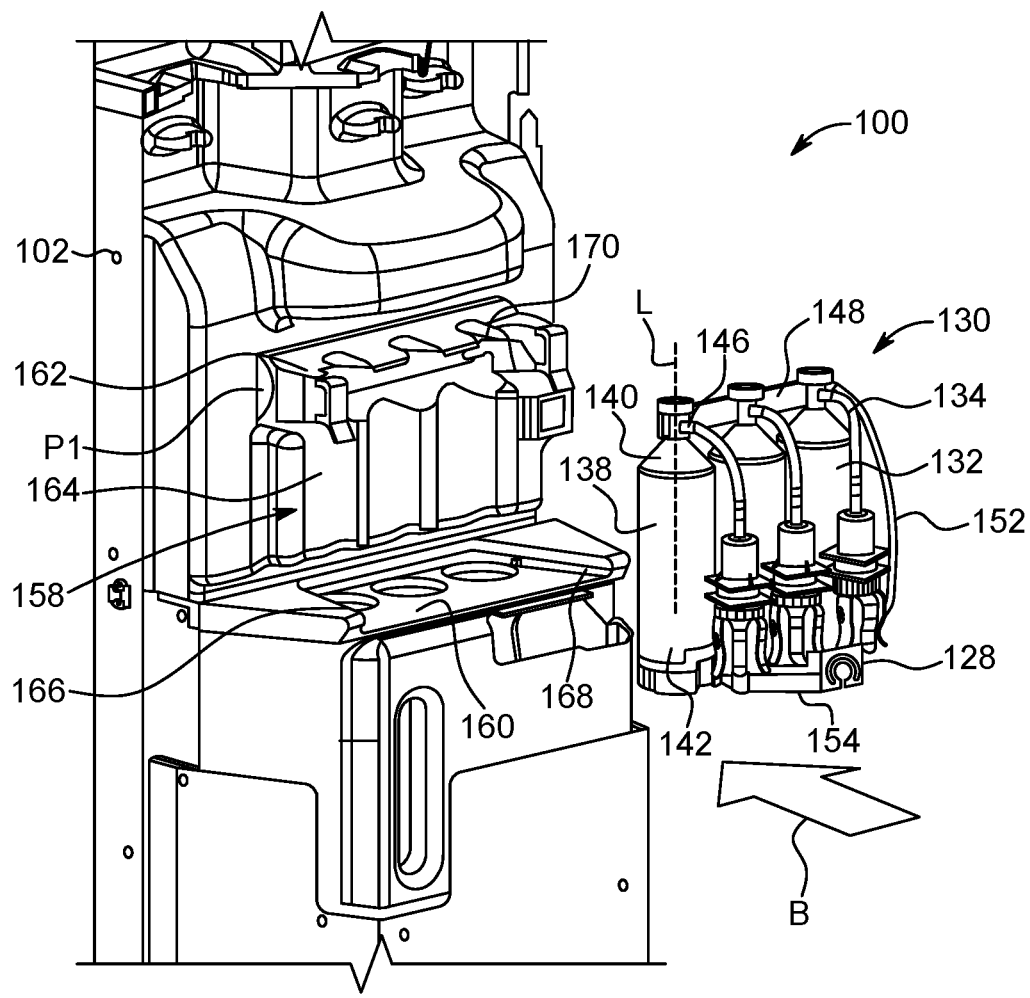
FIG. 3A is a perspective view of a multi-use disposable system as it is inserted into a receiving slot on a multi-fluid delivery system.
Figure 3B:
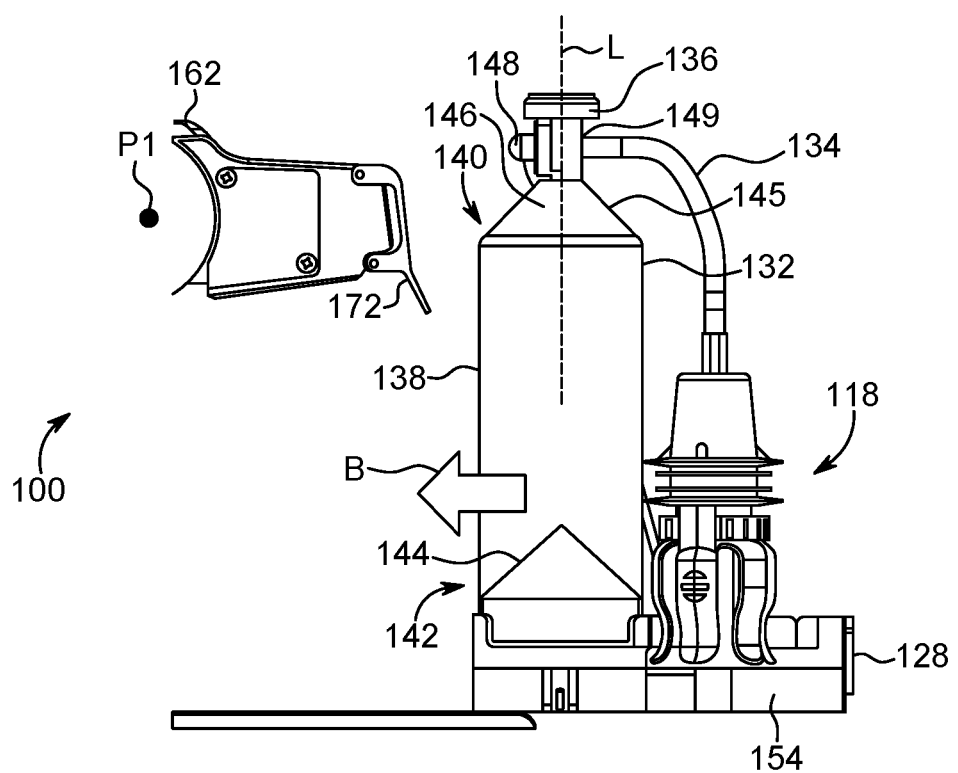
FIG. 3B is a side view of the multi-use disposable system of FIG. 3A.

With further reference to FIG. 3A, the MUDS 130 is removably connectable to the housing 102 of the fluid injector system 100. The MUDS 130 may include a frame 154 for supporting the one or more syringes 132. The syringes 132 may be removably or non-removably connected to the frame 154. In certain examples, the at least one syringe 132 may be co-molded with the frame 154 or alternatively, adhered or welded to the frame 154. With further reference to FIG. 3B, each syringe 132 has an elongated, substantially cylindrical syringe body 138 having a front or distal end 140 and a rear or proximal end 142. A syringe plunger 144 is disposed within the syringe body 138 and is reciprocally movable within the syringe body 138 due to movement of a piston 103 associated with the fluid injector system 100. The distal end 140 of the syringe body 138 is generally conical-shaped and tapers to an apex or cone point which is adapted to interface with a corresponding apex curve formed in the recess defined in the fluid injector system 100, as described herein. The syringe apex or cone point is located along a central longitudinal axis L of the syringe body 138. Each syringe 132 has a discharge outlet or conduit 146 at the terminal end of the apex or cone point. The discharge outlet 146 of each syringe 132 is in fluid communication with a valve 136 (shown in FIG. 2) which provides fluid communication with a manifold 148 and bulk fluid connector 118. The manifold 148 may also provide support for the syringes 132 along with the frame 154 so the syringes 132 can be handled as a single, unitary structure. In some examples, the manifold 148 supports the distal end 140 of each syringe 132 while the frame 154 supports the proximal end 142 of each syringe 132. The syringes 132 may be arranged in a side-by-side orientation, or any other orientation that retains the relative positioning of the syringes 132.

With specific reference to FIG. 2, a schematic view of various fluid paths of the fluid injector system 100 is provided. The MUDS 130 may include one or more valves 136, such as stopcock valves, for controlling which medical fluid or combinations of medical fluids are withdrawn from the multi-dose bulk fluid source 120 and/or are delivered to a patient through each syringe 132. In some examples, the one or more valves 136 may be provided on the distal end 140 of the plurality of syringes 132 or on the manifold 148. The manifold 148 may be in fluid communication via valves 136 and/or syringes 132 with a first end of the MUDS fluid path 134 that connects each syringe 132 to the corresponding bulk fluid source 120. The opposing second end of the MUDS fluid path 134 may be connected to the respective bulk fluid connector 118 that is configured for fluidly connecting with the bulk fluid source 120. Depending on the position of the one or more valves 136, fluid may be drawn into the one or more syringes 132, or it may be delivered from the one or more syringes 132. In a first position, such as during the filling of the syringes 132, the one or more valves 136 are oriented such that fluid flows from the bulk fluid source 120 into the desired syringe 132 through a fluid inlet line 150, such as the MUDS fluid path 134. During the filling procedure, the one or more valves 136 are positioned such that fluid flow through one or more fluid outlet lines 152 or the manifold 148 is blocked. In a second position, such as during a fluid delivery procedure, fluid from one or more syringes 132 is delivered to the manifold 148 through the one or more fluid outlet lines 152 or syringe valve outlet ports. In a third position, all fluid flow into and out of the one or more syringes 132 may be blocked, for example by having the one or more valves 136 turned to a position where there is not fluid communication between the interior of the syringe 132 and either the fluid inlet lines 150 or the one or more fluid outlet lines 512/manifold 148. During the delivery procedure, the one or more valves 136 are positioned such that fluid flow through one or more fluid inlet lines 150 is blocked. The one or more valves 136, fluid inlet lines 150, and/or fluid outlet lines 152 may be integrated into the manifold 148. The one or more valves 136 may be selectively positioned to the first, second, or third position by manual or automatic handling. For example, the operator may position the one or more valves 136 into the desired position for filling or fluid delivery. In other examples, at least a portion of the fluid injector system 100 is operable for automatically positioning the one or more valves 136 into a desired position for filling or fluid delivery based on input by the operator, as described herein.

With continued reference to FIG. 2, in some examples, the fluid outlet line 152 may also be connected to a waste reservoir 156 on the fluid injector system 100. The waste reservoir 156 is desirably separate from the syringes 132 to prevent contamination. In some examples, the waste reservoir 156 is configured to receive waste fluid expelled from the syringes 132 during, for example, a priming operation. The waste reservoir 156 may be removable from the housing 102 in order to dispose of the contents of the waste reservoir 156. In other examples, the waste reservoir 156 may have a draining port (not shown) for emptying the contents of the waste reservoir 156 without removing the waste reservoir 156 from the housing 102. In some examples, the waste reservoir 156 is provided as a separate component from the MUDS 130.

With the foregoing description of the fluid injector system 100 and the MUDS 130 in mind, exemplary loading of the MUDS 130 into a receiving space 158 (shown in FIG. 3A) on the housing 102 will now be described with reference to FIGS. 3A-4B. In the following discussion, it is assumed that the MUDS 130 may be connected to and removed from connection with the fluid injector system 100 for use with a single or multiple patients. Referring initially to FIG. 3A, the receiving space 158 has a bottom plate 160 separated from a top plate 162 by a rear sidewall 164. The bottom plate 160 has a plurality of openings 166 through which the pistons 103 (shown in FIG. 2) of the fluid injector system 100 extend to engage the respective plungers 144 of the MUDS 130. At least one bottom guide 168 is formed on the bottom plate 160 for guiding the frame 154 of the MUDS 130 as the MUDS 130 is loaded into the fluid injector system 100. In some examples, the bottom guide 168 may be configured as a pair of walls raised relative to the bottom plate 160 and narrowing in an insertion direction toward the rear sidewall 164. During insertion of the MUDS 130, in the direction of arrow B, the bottom guide 168 defines a guiding surface that locates the frame 154 of the MUDS 130 and guides the frame 154 toward the rear sidewall 164 of the receiving space 158. In this manner, the MUDS 130 can be aligned into the receiving space 158 even when the MUDS 130 is initially misaligned with the receiving space 158.

With reference to FIG. 3B, and with continued reference to FIG. 3A, the top plate 162 is configured to receive the distal end 140 of the at least one syringe 132. The top plate 162 has one or more syringe slots 170 (shown in FIG. 3A) that are shaped to receive at least a portion of the distal end 140 of the syringes 132. In some examples, when the MUDS 130 is inserted into the receiving space 158, the syringe slots 170 of the top plate 162 may be disposed between the distal end 140 of the at least one syringe 132 and the manifold 148. The top plate 162 may be rotatable about a pivot point P1, shown in FIG. 3B, or it may be movable in a vertical direction relative to the MUDS 130. In a first position, such as during loading of the MUDS 130 into the receiving space 158, the top plate 162 may be raised such that the apex or cone point 145 of the at least one syringe 132 clears a lower surface of the top plate 162. In some examples, the top plate 162 can default to the first position each time the MUDS 130 is removed from the receiving space 158, such as by a biasing mechanism. In other examples, the top plate 162 can be urged to the first position as the apex or cone point 145 of the at least one syringe 132 engages the at least one syringe slot 170.

Figure 4A:
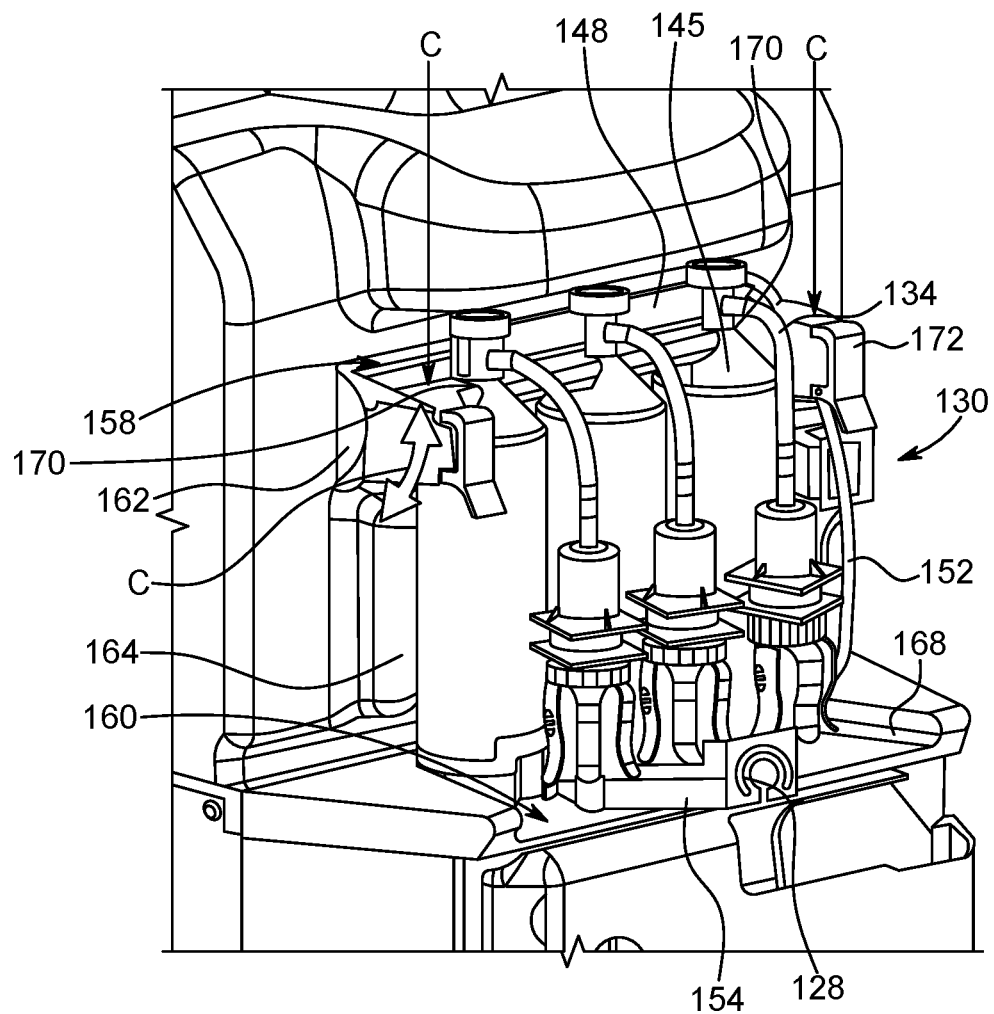
FIG. 4A is a perspective view of the multi-use disposable system installed into a receiving slot on the multi-fluid delivery system of FIG. 3A.
Figure 4B:
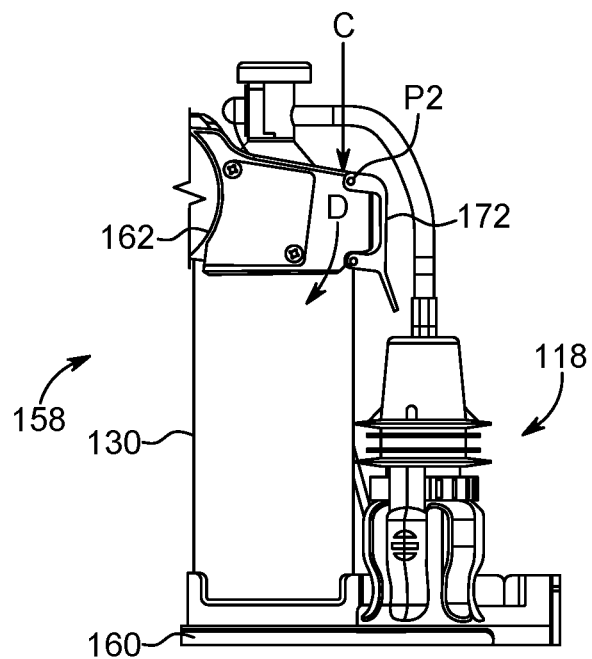
FIG. 4B is a side view of the multi-use disposable system of FIG. 4A.
Figure 4C:
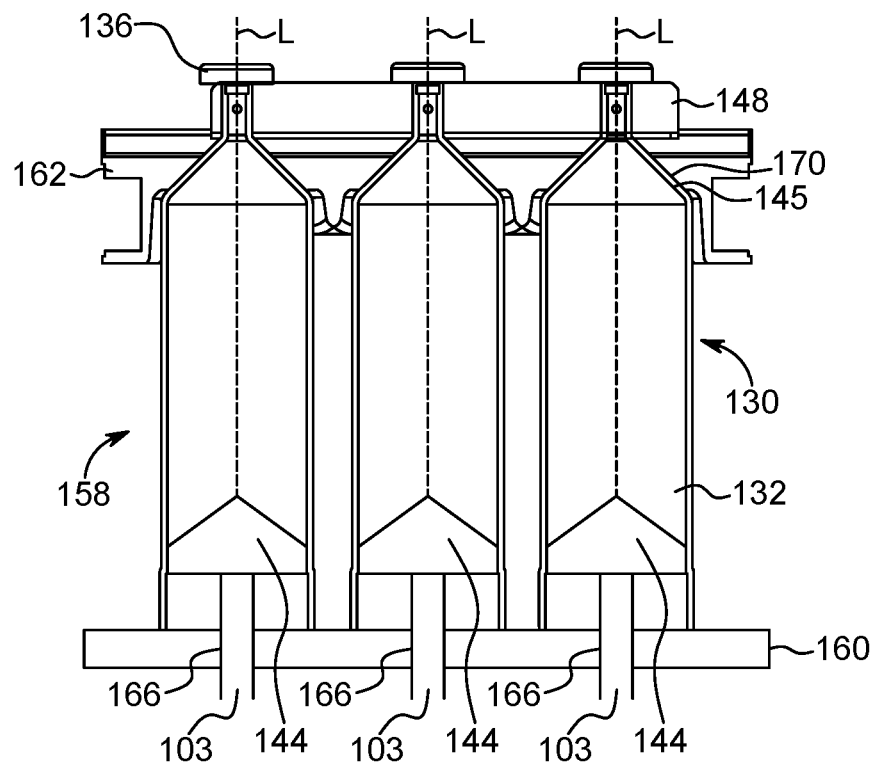
FIG. 4C is a side cross-sectional view of the multi-use disposable system of FIG. 4A.

As the MUDS 130 engages the rear sidewall 164, such as shown in FIG. 4A, the MUDS 130 can be locked in the receiving space 158 by moving the top plate 162 to a second position. In the second position, the top plate 162 is lowered such that the apex or cone point 145 of the at least one syringe 132 engages the lower surface of the top plate 162. In some examples, the top plate 162 can be urged to the second position by a biasing mechanism (not shown). In other examples, the top plate 162 can be manually or automatically moved between the first position and the second position by pivoting the top plate 162 in a direction of arrow C shown in FIGS. 4A-4B. The top plate 162 can be locked relative to the MUDS 130 to prevent removal of the MUDS 130 from the receiving space 158 by a latch 172. The latch 172 may be operable to prevent the top plate 162 from rotating about the pivot point P1. The latch 172 may be a spring-loaded latch that is pivotable about a pivot point P2 in a direction of arrow D shown in FIG. 4B. In some examples, the latch 172 may be an over-center, spring-loaded latch that is pivotable about a pivot point P2. With reference to FIG. 4C, when the MUDS 130 is locked within the receiving space 158, the lower surface of the top plate 162 engages the apex or cone point 145 of the at least one syringe 132. In the locked position, the longitudinal axis L of each syringe 132 is aligned with a center of each syringe slot 170. Removal of the MUDS 130 from the receiving space 158 when the top plate 162 is in the locked position is prevented by the engagement of the lower surface of the top plate 162 with the apex or cone point 145 of the at least one syringe 132. Once locked, the top plate 162 substantially retains the syringes 132 from moving axially during an injection procedure.

With reference to FIG. 4C, during an injection procedure, the one or more pistons 103 of the fluid injector system 100 extend through the openings 166 on the bottom plate 160 to engage the respective plungers 144 of the MUDS 130. Each piston 103 is configured to releasably connect to the respective plunger 144 in order to allow the plunger to be moved in a proximal and distal direction within the barrel of each syringe 132. As described herein, a syringe engagement mechanism may be provided for releasably connecting the pistons 103 to the respective plungers 144.

Once the injection procedure is completed, the MUDS 130 may be removed from the receiving space 158 by unlocking the top plate 162 from the apex or cone point or conical portion 145 of the at least one syringe 132. In some examples, the top plate 162 is unlocked by unlatching the latch 172 through a pivoting movement of the latch 172 about the pivot point P2. As the latch 172 is unlatched, the top plate 162 is pivoted upwards relative to the MUDS 130. By unlocking the top plate 162, the top plate 162 can be moved (i.e., pivoted or raised) relative to the MUDS 130 to allow the apex or cone point or conical portion 145 of the at least one syringe 132 to clear the syringe slot 170 (shown in FIG. 3A) of the top plate 162. The MUDS 130 can then be extracted in a direction opposite the insertion direction B by moving the MUDS 130 away from the rear sidewall 164 (shown in FIG. 3A). Examples and features of the MUDS are further described in International Application Publication No. WO 2016/112163, filed on Jan. 7, 2016, the disclosure of which is incorporated herein by reference in its entirety. Prior to or concurrent with MUDS 130 removal, the one or more pistons 103 of the injector are disengaged from the one or more plungers and retracted to the initial proximal position.

Figure 5:
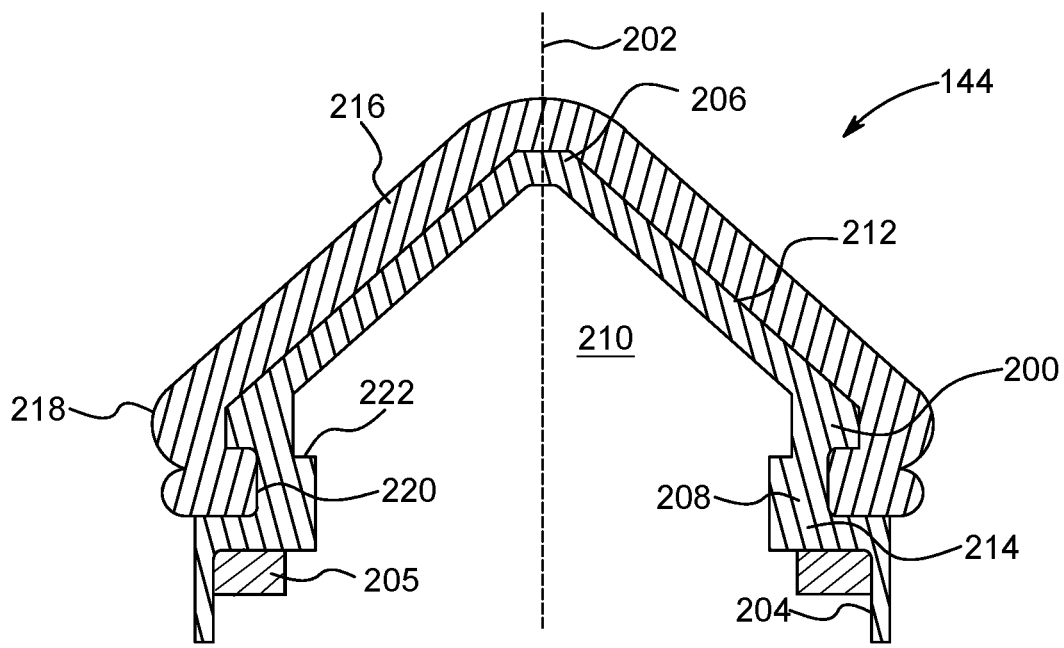
FIG. 5 is a side cross-sectional view of a plunger for use with a syringe of the multi-use disposable system in accordance with one example of the present disclosure.

With reference to FIG. 5, the plunger 144 is shown in accordance with one example of the present disclosure. Other suitable plunger configurations are described in U.S. Application Publication No. US2017/0043082 and for example with a dynamic seal that may be suitable for use in the MUDS 130 of the present disclosure are described in International Application Publication No. WO 2018/129116, filed Jan. 4, 2018, the disclosure of which is incorporated herein by this reference in its entirety. The barrel of the syringe 132 is omitted from FIG. 5 for clarity. The plunger 144 includes a plunger body 200 having a plunger longitudinal axis 202, a proximal end 204, a distal end 206, and a circumferential sidewall 208 connecting the proximal end 204 and the distal end 206. The sidewall 208 may have a uniform or non-uniform thickness between the proximal end 204 and the distal end 206. The sidewall 208 may have a continuous or discontinuous outer surface. The plunger body 200 may be formed from glass, metal, plastic, or other suitable material, including medical grade versions.

With continued reference to FIG. 5, the plunger body 200 has an interior cavity 210 defined by a conical-shaped portion 212 at the distal end 206 of the plunger body 200 and a cylindrical-shaped portion 214 at the proximal end 204 of the plunger body 200. The conical-shaped portion 212 may be monolithically formed with the cylindrical-shaped portion 214. In some examples, the conical-shaped portion 212 may be affixed or otherwise secured to the cylindrical-shaped portion 214 of the plunger body 200 using, for example, a frictional fit and/or an adhesive, welding, or by molding. The conical-shaped portion 212 may be truncated at the distal end 206.

With continued reference to FIG. 5, the plunger body 200 may have a resilient plunger cover 216 that covers at least a portion of an outer surface of the plunger body 200. A seal 218 may be provided on the plunger cover 216 at an interface between the plunger cover 216 and the inner surface of the syringe barrel. The seal 218 may be a resilient and flexible seal that engages the inner surface of the syringe barrel such that the seal 218 seals the interior volume of the syringe barrel in a liquid-tight manner. The plunger cover 216 may be provided separately from the plunger body 200, or it may be integrally formed with the plunger body 200, such as by co-molding. In some examples, the outer surface of the plunger body 200 may have a circumferential groove 220 such that at least a portion of the plunger cover 216 is retained within the circumferential groove 220.

With continued reference to FIG. 5, the plunger 144 has at least one radially inward facing pin engagement surface 222 (hereinafter referred to as "pin engagement surface 222") on an inside surface thereof. The pin engagement surface 222 may be formed as a groove that is recessed in a radially outward direction into the inside surface of the plunger body 200. The pin engagement surface 222 may extend around at least a portion of the inner circumference of the plunger body 200. In some examples, the pin engagement surface 222 is circumferentially continuous around the entire inner circumference of the plunger body 200. In other examples, the pin engagement surface 222 may be comprised from one or more discrete circumferential segments. The pin engagement surface 222 is configured to interact with at least a portion of the piston 103, such as the plunger engagement mechanism described herein, to enable the plunger 144 to be releasably locked with the piston 103 such that the plunger 144 can be driven reciprocally within the barrel of the syringe 132 via movement of the piston 103. In certain embodiments, the pin engagement surface 222 may include a plurality of bracing features 205 to strengthen pin engagement surface 222 against proximal forces when the piston 103 is retracted in the proximal direction.

Figure 6:
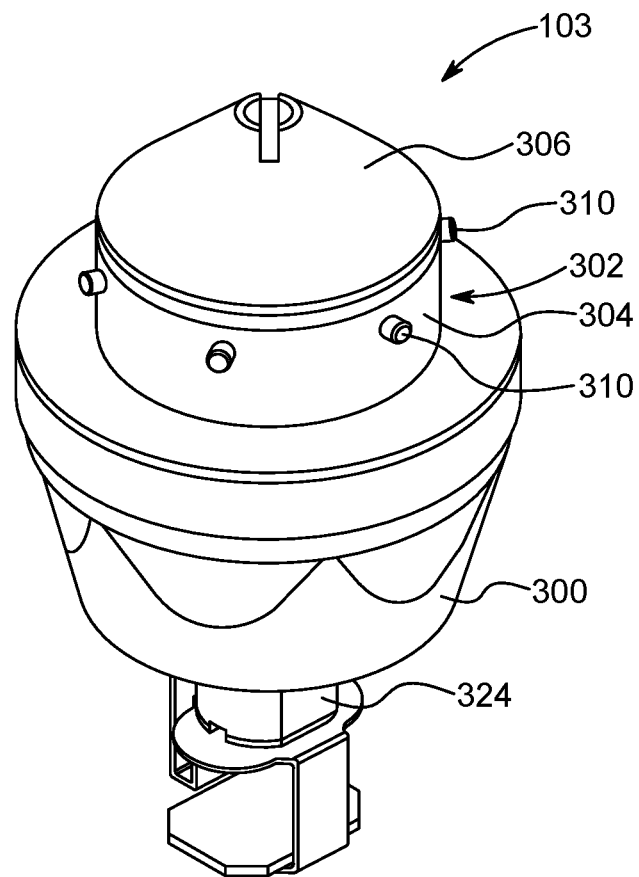
FIG. 6 is a perspective view of a piston of a multi-fluid delivery system in accordance with one example of the present disclosure.
Figure 7:
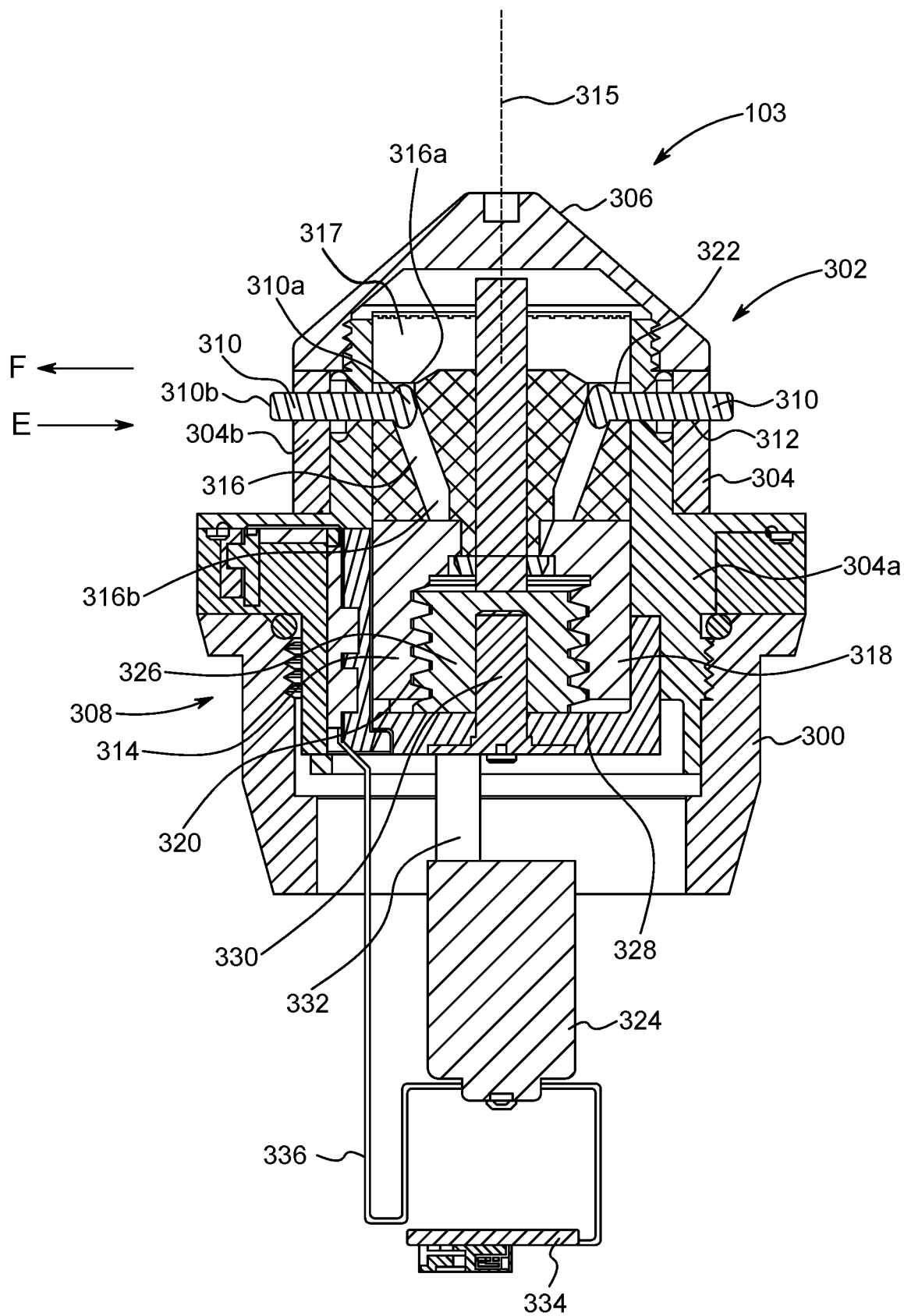
FIG. 7 is a side cross-sectional view of the piston shown in FIG. 6.

Referring to FIGS. 6-7, the piston 103 is shown separate from the fluid injector system 100 (shown in FIG. 1). The piston 103 is configured to interact with the plunger 144 (shown in FIGS. 8A-8B) to releasably lock the plunger 144 such that the plunger 144 can be driven reciprocally within the barrel of the syringe 132 via movement of the piston 103. The piston 103 is extendible and retractable from the housing 102 of the fluid injector system 100 via a powered means (not shown) preferably contained within housing 102. The powered means may include, for example, an electric motor, a hydraulic system, or a pneumatic system, including appropriate gearing (not shown).

With continued reference to FIGS. 6-7, the piston 103 includes a stem 300 and a piston head 302 formed on a distal end of the stem 300 such that at least a portion of the piston head 302 extends distally from the stem 300. The piston 103 is constructed from a rigid material, such as metal or plastic that resists deformation. The piston head 302 may have a substantially cylindrical proximal end 304 with a pointed distal end 306. The proximal end 304 and the distal end 306 may be removably or non-removably connected to each other. For example, as shown in FIG. 7, the proximal end 304 may be threadably connected with the distal end 306 to establish a removable connection therebetween. The proximal end 304 and the distal end 306 of the piston head 302 are shaped to be received inside at least a portion of an interior cavity 210 of the plunger 144 (shown in FIG. 5). In some examples, the proximal end 304 may have an inner portion 304a disposed within an outer portion 304b. The piston 103 may be hollow such that an interior cavity 317 is defined in at least a portion of the piston 103.

Figure 8A:
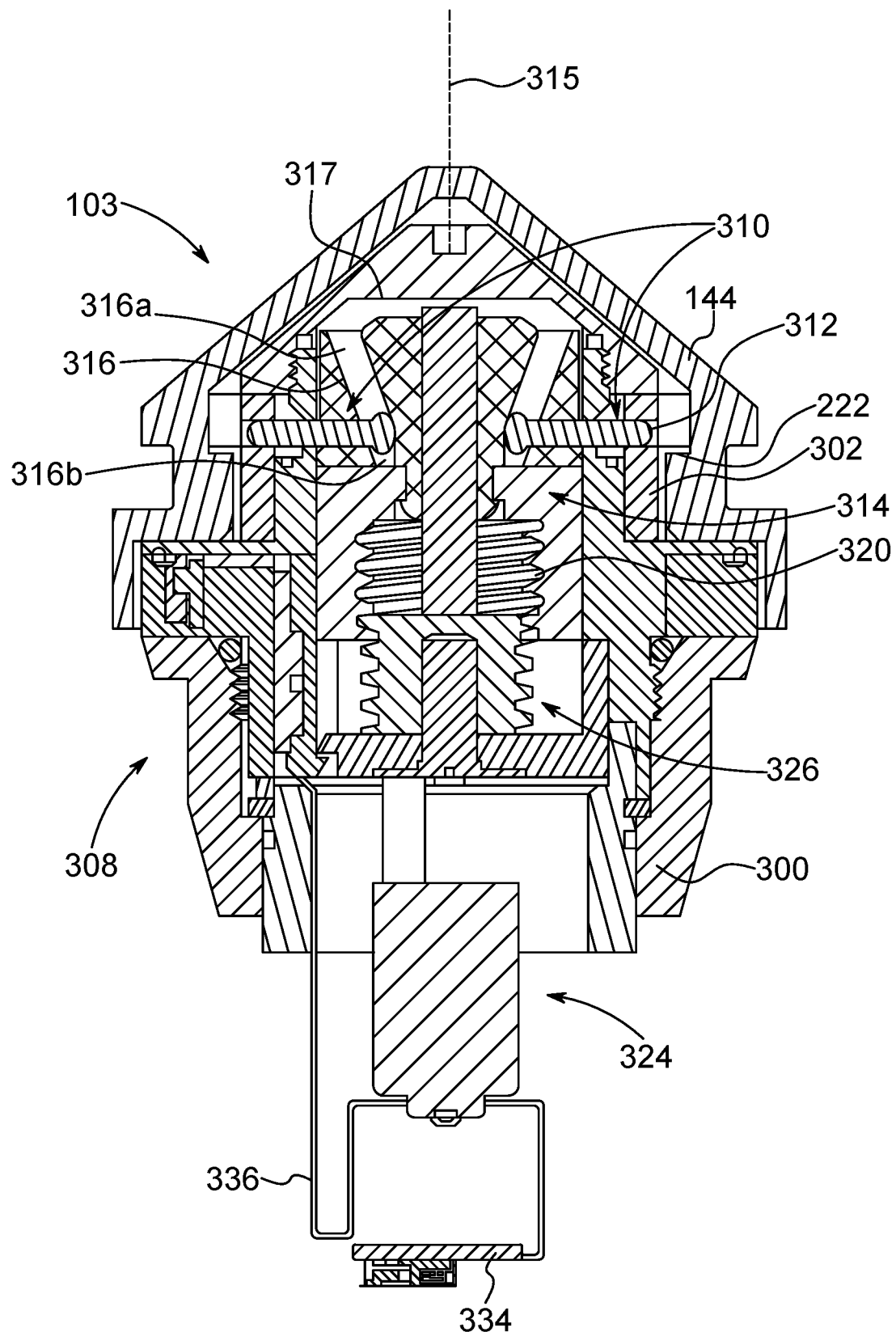
FIG. 8A is a side cross-sectional view of a piston and a plunger with a plunger engagement mechanism of the piston shown in a disengaged position.
Figure 8B:
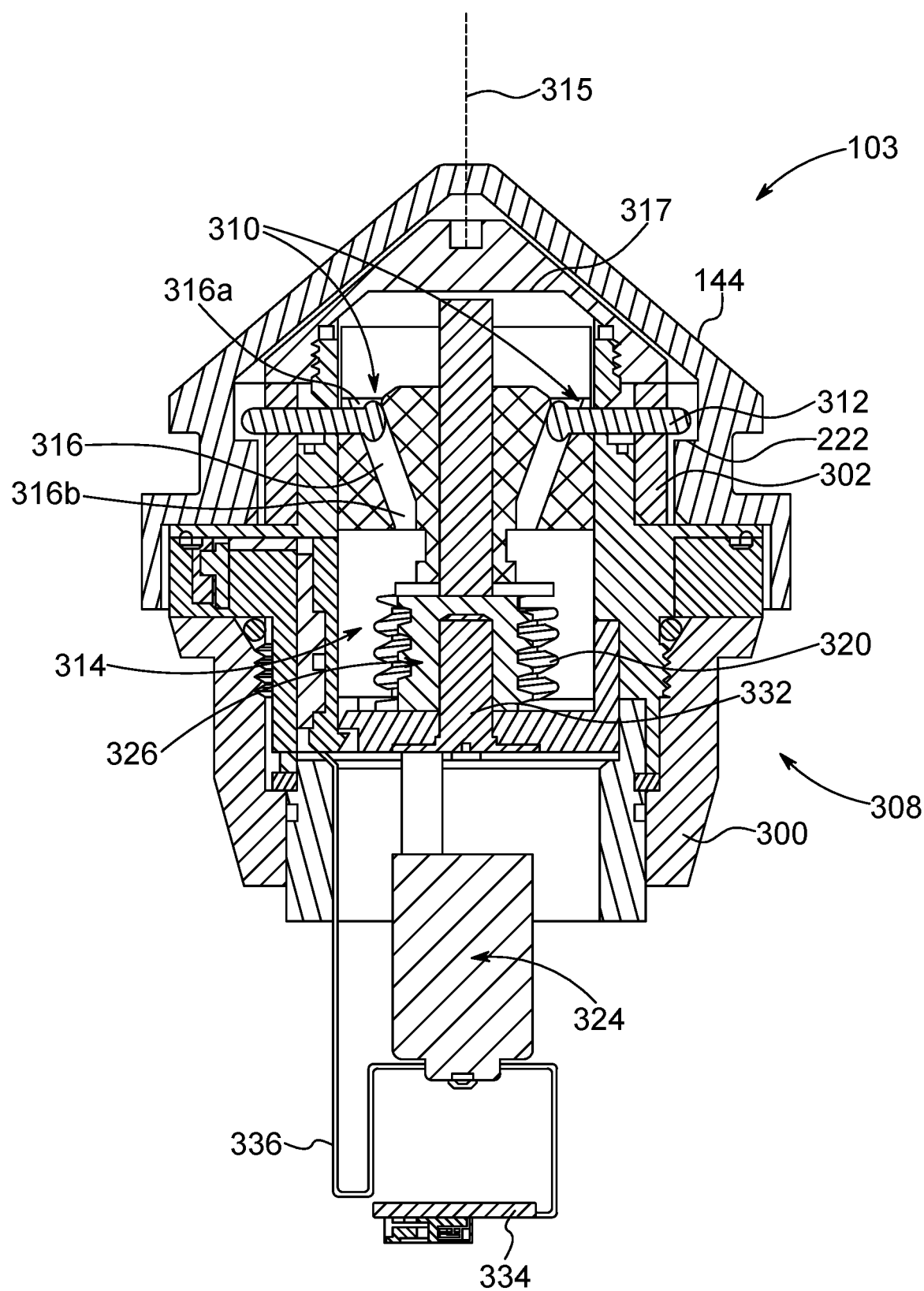
FIG. 8B is a side cross-sectional view of the piston and plunger shown in FIG. 8A with the plunger engagement mechanism shown in an engaged position.

In certain embodiments, the piston head 302 may have a plunger engagement mechanism 308 (shown in FIG. 7) that is configured to interact with the plunger 144 to releasably engage with the plunger 144, such as shown in FIGS. 8A-8B. By engaging the piston 103 with the plunger 144, the plunger 144 can be driven reciprocally within the barrel of the syringe 132. The plunger engagement mechanism 308 may have one or more pins 310 that are reversibly movable radially relative to the piston head 302. For example, the one or more pins 310 may be movable between a first or withdrawn position, wherein the one or more pins 310 are radially withdrawn into the piston head 302; and a second or extended position, wherein the one or more pins 310 protrude radially outward relative to an outer surface of the piston head 302, such as the outer surface of the proximal end 304. The one or more pins 310 may move through corresponding openings 312 on the piston head 302. One or more o-rings 319 may be associated with each pin to prevent fluid ingress into the engagement mechanism. Additional o-rings 319a and gaskets 319b may be associated with various locations along the piston to prevent fluid ingress into the engagement mechanism (see FIG. 10). For example, the one or more pins 310 may be movable radially inward in a direction of arrow E and radially outward in a direction of arrow F (FIG. 7) through corresponding openings 312 on the proximal end 304 of the piston head 302, to disengage and engage the plunger 144, respectively. The one or more pins 310 are configured to engage the pin engagement surface 222 on the plunger 144 when the one or more pins 310 are in the second or extended position. In some examples, the one or more pins 310 have a substantially circular cross-sectional shape. In other examples, the one or more pins 310 may have any other regular or irregular geometric shape, for example a square cross-section, rectangular cross-section or any other polyhedral cross-section. In further examples, each pin 310 may have a bulbous first end 310a that is received within the piston 103 and a substantially prismatic second end 310b shaped to extend through the corresponding openings 312 on the piston head 302.

With reference to FIG. 7, according to certain embodiments the plunger engagement mechanism 308 has a cam sleeve 314 movably disposed within an interior cavity 317 of the piston 103 relative to a cam surface 314a. The can sleeve 314 is movable in a proximal or distal direction along a longitudinal axis 315 of the piston 103 due to actuation of an actuator 324, as described herein. The cam sleeve 314 has a proximal end 318 having a threaded interface 320 and a distal end 322 having one or more tracks 316. The threaded interface 320 may have a male or a female thread and is configured for threaded engagement with at least a portion of a female or male thread of the actuator 324. The cam sleeve 314 is linearly, reversibly movable within the interior cavity 317 via a rotational engagement between the threaded interface 320 on the proximal end 318 and at least a portion of the actuator 324.

With continued reference to FIG. 7, each track 316 of cam sleeve 314 may be configured to receive at least a portion of one of the pins 310. For example, each track 316 may receive the bulbous first end 310a of each pin 310. The one or more tracks 316 are angled relative to the longitudinal axis 315 of the piston 103 and define a cam surface for engagement with the corresponding pins 310. In some examples, the one or more tracks 316 have a diagonally linear shape. In other examples, the one or more tracks 316 have an arcuate shape. The one or more tracks 316 are arranged such that the one or more tracks 316 diverge from the longitudinal axis 315 in a proximal to distal direction. That is, a distal end 316a of each track 316 is radially farther from the longitudinal axis 315 than a proximal end 316b of each track 316. Movement of the cam sleeve 314 relative to the plunger head 302 in a distal direction along the longitudinal axis 315 may cause the pins 310 to move from a distal end 316a of the tracks 316 toward a proximal end 316b such that the pins 310 are withdrawn into the openings 312 on the plunger head 302 (FIG. 8A). Conversely, movement of the cam sleeve 314 in a proximal direction may cause the pins 310 to move from the proximal end 316b of the tracks 316 toward the distal end 316a such that the pins 310 are extended radially outward from the openings 312 on the plunger head 302 (FIG. 8B). It should be understood that in other embodiments, the direction of the one or more tracks 316 could be inverted converge and from the longitudinal axis 315 in a proximal to distal direction. Movement of the cam sleeve 314 relative to the plunger head 302 in a proximal direction along the longitudinal axis 315 may cause the pins 310 to move from a distal end 316a of the tracks 316 toward a proximal end 316b such that the pins 310 are extended out of the openings 312 on the plunger head 302 (FIG. 8A).

It should be understood that in other embodiments, the direction of the one or more tracks 316 could be inverted, such that the one or more tacks 316 converge toward the longitudinal axis 315 in a proximal to distal direction. That is, the distal end 316a of each track 316 is radially closer to the longitudinal axis 315 than the proximal end 316b of each track 316. Movement of the cam sleeve 314 relative to the plunger head 302 in a distal direction along the longitudinal axis 315 may cause the pins 310 to move from the distal end 316a of the tracks 316 toward the proximal end 316b such that the pins 310 are extended radially outward from the openings 312 on the plunger head 302 (FIG. 8A). Conversely, movement of the cam sleeve 314 in a proximal direction may cause the pins 310 to move from the proximal end 316b of the tracks 316 toward the distal end 316a such that the pins 310 are withdrawn into the openings 312 on the plunger head 302.

With continued reference to FIG. 7, the proximal end 318 of the cam sleeve 314 is in a threaded attachment with a screw 326 driven by the actuator 324. The screw 326 is shaped such that the threads 328 of the screw 326 mesh with the threaded interface 320 of the proximal end 318 of the cam sleeve 314. While FIG. 7 shows a male-threaded screw 326 that is threadably engaged with the female-threaded interface 320, this arrangement can be reversed such that the screw 326 is female threaded while the threaded interface 320 has a corresponding male thread. The screw 326 is connected to the actuator 324 by a drive shaft 330, which is in turn connected to an output shaft 332 of the actuator 324. In some examples, the output shaft 332 of the actuator 324 may be directly connected to the screw 326, for example through proximal end 339. Rotation of the output shaft 332 of the actuator 324 rotates the screw 326 about the longitudinal axis 315, which in turn linearly moves the cam sleeve 314 within the interior cavity 317 of the plunger head 302. In this manner, the actuator 324 is configured for moving the cam sleeve 314 between the first position and the second position (FIGS. 8A-8B, respectively). In some examples, the actuator 324 may be a rotary electric motor. In the example shown in FIG. 7, the actuator 324 is a rotary electric motor having the output shaft 332 that is rotatable about the longitudinal axis 315.

The actuator 324 is operatively connected to a controller 334 for controlling rotary motion of the actuator 324. For example, the actuator 324 may be connected to the controller 334 by wiring 336 that sends control signals from the controller 334 to the actuator 324 to control operation of the actuator 324. In other examples, the actuator 324 may be wirelessly connected to the controller 334. The controller 334 may instruct the actuator 324 to rotate in the appropriate direction, for example clockwise or counterclockwise, to engage or disengage the plunger depending on the signal received from the controller 334. In other embodiment, the actuator 324 may only rotate in one direction and gearing (not shown) may be used to rotate the screw 326 in either the clockwise or counterclockwise directions.

Figure 9:
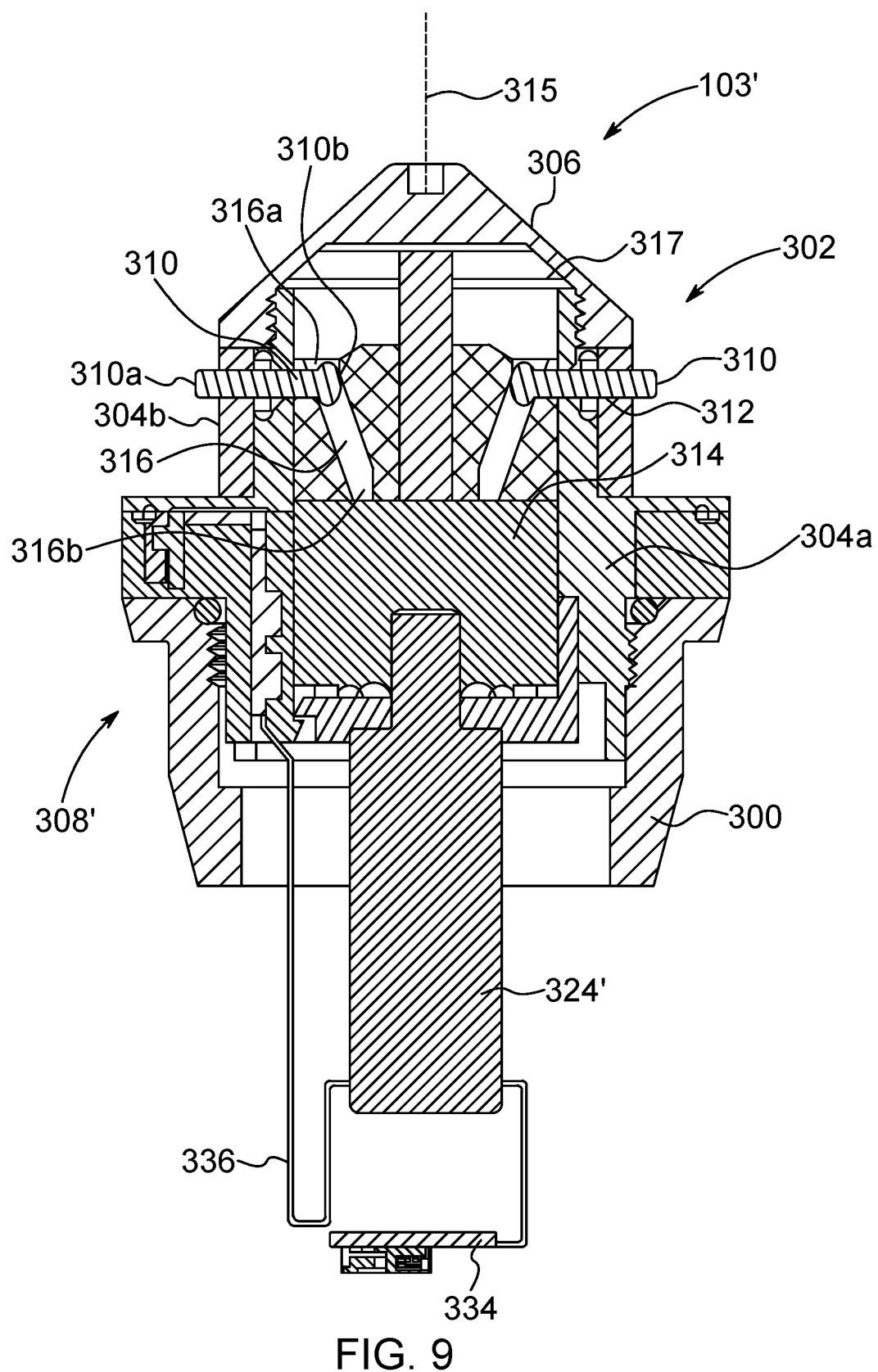
FIG. 9 is a side cross-sectional view of a piston of a multi-fluid delivery system in accordance with another example of the present disclosure.

With reference to FIG. 9, an embodiment of a piston 103' is shown in accordance with another example. The components of the piston 103' shown in FIG. 9 are substantially similar to the components of the piston 103 described herein with reference to FIGS. 6-8B. Reference numerals in FIG. 9 are used to illustrate identical components of the corresponding reference numerals in FIGS. 6-8B. As the previous discussion regarding the piston 103 generally shown in FIGS. 6-8B is applicable to the piston 103' shown in FIG. 9, only the relative differences between the piston 103 shown in FIGS. 6-8B and the piston 103' shown in FIG. 9 are discussed hereinafter.

Whereas the plunger engagement mechanism 308 described herein with reference to FIGS. 6-8B has an actuator 324 configured for rotary movement, the actuator 324' shown in FIG. 9 is configured for linear movement in a direction along the longitudinal axis 315. In some examples, the actuator 324' may be a linear electric motor, a linear actuator, a solenoid, rack-and-pinion, or the like. The actuator 324' is connected to the cam sleeve 314 such that linear movement of the actuator 324' in a direction along the longitudinal axis 315 results in a corresponding linear movement of the cam sleeve 314 within the interior cavity 317 of the piston 103. In particular, the cam sleeve 314 is movable in a proximal/distal direction along a longitudinal axis 315 of the piston 103 due to linear movement of the actuator 324'. In some examples, the proximal end 318 of the cam sleeve 314 may be removably connected to the actuator 324', such as by way of a threaded attachment. As described herein with reference to FIGS. 6-8B, movement of the cam sleeve 314 relative to the plunger head 302 in a distal direction along the longitudinal axis 315 may cause the pins 310 to move from a distal end 316a of the tracks 316 toward a proximal end 316b such that the pins 310 are withdrawn into the openings 312 on the plunger head 302. Conversely, movement of the cam sleeve 314 in a proximal direction may cause the pins 310 to move from the proximal end 316b of the tracks 316 toward the distal end 316a such that the pins 310 are extended radially outward from the openings 312 on the plunger head 302. As before, it should be understood that in other embodiments, the direction of the one or more tracks 316 could be inverted such that the one or more tracks 316 converge towards the longitudinal axis 315 in a proximal to distal direction. Consequently, in such embodiments, movement of the cam sleeve 314 relative to the plunger head 302 in a distal direction would cause the pins 310 to extend radially outward, and movement of the cam sleeve 314 relative to the plunger head 302 in a proximal direction would cause the pins 310 to be withdrawn.

In some examples, the plunger engagement mechanism may be similar or identical to the plunger engagement mechanism shown in FIGS. 46E and 47E of U.S. Pat. No. 8,945,051, the disclosure of which is incorporated by reference herein in its entirety. For example, the plunger engagement mechanism may have a rotational solenoid or a linear solenoid configured for selectively moving at least one pin into an interference engagement between the syringe plunger and the piston.

Having described the structure of the at least one piston 103 and the corresponding plunger engagement mechanism 308, the locking or engagement of the at least one piston 103 to the corresponding plunger 144, and the unlocking or disengagement of the at least one piston 103 from the corresponding plunger 144 will be described herein according to one embodiment with reference to FIGS. 8A-8B and exploded view in FIG. 10.

To engage or lock the plunger 144 with the piston 103 after the MUDS has been loaded into the fluid injector 100, the piston 103 is advanced distally in a direction of longitudinal axis 315 until the distal end of the piston 103 contacts the interior surface of the distal end of the plunger 144. The plunger 144 may be positioned at the proximal end of the syringe barrel, at the distal end of the syringe barrel, or at any axial position between the proximal end and the distal end of the syringe barrel. In some aspects, the piston 103 may be advanced distally toward the plunger 144 by way of the powered means, such as an electric motor (not shown). In other examples, the piston 103 may be advanced distally toward the plunger 144 by manual operation. A sensor (not shown) may be used to stop the distal movement of the piston 103 once the sensor detects that the piston 103 is in contact with the distal end of the plunger 144. Alternatively, the piston 103 may contact the plunger 114 and advance it distally until the plunger 114 contacts the distal conical inner surface 145 of the syringe 132, which may be sensed, for example, by the sensor or by an increase in the countering force as the plunger contacts the distal surface 145 of the syringe. With the piston 103 positioned for locking with the plunger 144 (FIG. 8A), the actuator 324 is actuated to move the screw 326, such as by rotating the screw 326 in a first direction (clockwise or counterclockwise) relative to the longitudinal axis 315 via movement of the output shaft 332.

Movement of the screw 326 causes a corresponding movement of the cam sleeve 314 within the interior cavity 317 of the plunger head 302 due to engagement between the threads of the screw 326 with the threads of the threaded interface 320 on the cam sleeve 314. In particular, rotation of the screw 326 in the first direction may cause a linear movement of the cam sleeve 314 in a first direction, such as a proximal direction. Conversely, rotation of the screw 326 in a second direction opposite the first direction, such as a counterclockwise or clockwise direction about the longitudinal axis 315, may cause a linear movement of the cam sleeve 314 in a second direction opposite the first direction, such as a distal direction.

With examples having the actuator 324' configured for linear rather than rotational movement, such as shown in FIG. 9, movement of the actuator 324' in a distal direction along the longitudinal axis 315 moves the cam sleeve 314 distally relative to the plunger head 302, thereby moving the pins 310 from the distal end 316a of the tracks 316 toward the proximal end 316b such that the pins 310 are withdrawn into the openings 312 on the plunger head 302 into a first, withdrawn or disengaged position. Conversely, movement of the actuator 324' in a proximal direction along the longitudinal axis 315 moves the cam sleeve 314 proximally relative to the plunger head 302, thereby moving the pins 310 from the proximal end 316b of the tracks 316 toward the distal end 316a such that the pins 310 are extended radially outward from the openings 312 on the plunger head 302 into a second, extended or engaged position.

With reference to FIG. 8B, and with continued reference to FIG. 8A, proximal movement of the cam sleeve 314 within the interior cavity 317 of the plunger head 302 due to interaction of the threaded interface 320 with the screw 326 may cause the pins 310 to move from the proximal end 316b of the tracks 316 toward the distal end 316a such that the pins 310 are extended radially outward from the openings 312 on the plunger head 302 into a second, extended or engaged position. In the extended position shown in FIG. 8B, the pins 310 are configured to engage the pin engagement surface 222 on the plunger 144 such that the plunger 144 can be moved in the proximal direction with proximal movement of the piston 103. A plunger detection pin 325 may be aligned along the longitudinal axis and protrude from the distal end 306 to detect a presence of a plunger.

To disengage or unlock the plunger 144 from the piston 103 in order to remove the MUDS from the fluid injector 100, the actuator 324 is actuated to move the screw 326, such as by rotating the screw 326 in the second direction opposite the first direction via movement of the output shaft 332. Movement of the screw 326 causes a corresponding movement of the cam sleeve 314 within the interior cavity 317 of the plunger head 302 due to engagement between the threads of the screw 326 with the threads of the threaded interface 320 on the cam sleeve 314. In particular, rotation of the screw 326 in the second direction may cause a linear movement of the cam sleeve 314 in the second direction, such as a distal direction. A distal movement of the cam sleeve 314 within the interior cavity 317 of the plunger head 302 due to interaction of the threaded interface 320 with the screw 326 may cause the pins 310 to move from the distal end 316a of the tracks 316 toward the proximal end 316b such that the pins 310 are withdrawn in a radially inward direction from the openings 312 on the plunger head 302 into a first, withdrawn or disengaged position. In the withdrawn position shown in FIG. 8A, the pins 310 are disengaged from the pin engagement surface 222 on the plunger 144 such that the plunger 144 can be removed from the piston 103 to allow for removal of the MUDS once the piston 103 is proximally retracted from the interior of the syringe, leaving the plunger 144 remaining in the syringe.

In examples having the actuator 324' configured for linear rather than rotational movement, such as shown in FIG. 9, movement of the actuator 324' in a distal direction along the longitudinal axis 315 moves the cam sleeve 314 distally relative to the plunger head 302, thereby moving the pins 310 from the distal end 316a of the tracks 316 toward the proximal end 316b such that the pins 310 are withdrawn into the openings 312 on the plunger head 302 into a first, withdrawn or disengaged position. Conversely, movement of the actuator 324' in a proximal direction along the longitudinal axis 315 moves the cam sleeve 314 proximally relative to the plunger head 302, thereby moving the pins 310 from the proximal end 316b of the tracks 316 toward the distal end 316a such that the pins 310 are extended radially outward from the openings 312 on the plunger head 302 into a second, extended or engaged position.

While several examples of syringe plunger engagement mechanisms are shown in the accompanying drawings and described hereinabove in detail, other examples will be apparent to, and readily made by, those skilled in the art without departing from the scope and spirit of the disclosure. For example, it is to be understood that this disclosure contemplates that, to the extent possible, one or more features of any example can be combined with one or more features of any other example. Accordingly, the foregoing description is intended to be illustrative rather than restrictive.

We claim:

1. A fluid injector system comprising:
   at least one reciprocally operable piston having a piston head; and
   a plunger engagement mechanism associated with the piston head, the plunger engagement mechanism comprising:
      a cam sleeve disposed within the piston head and movable relative to the piston head, the cam sleeve having one or more tracks defining a cam surface;
      an actuator operatively connected to the cam sleeve for moving the cam sleeve relative to the piston head; and
      one or more pins at least partially disposed within the cam sleeve and movable within the one or more tracks with movement of the cam sleeve between a first, disengaged position, wherein the one or more pins are radially withdrawn into the piston head and a second, engaged position, wherein the one or more pins protrude radially outward relative to an outer surface of the piston head.

2. The fluid injector system of claim 1, wherein the piston head comprises one or more openings through which the one or more pins are movable between the first, disengaged position and the second, engaged position.

3. The fluid injector system of claim 1, wherein the one or more pins are configured to engage a pin engagement surface on a portion of a plunger when the one or more pins are in the second, engaged position.

4. The fluid injector system of claim 1, wherein the cam sleeve has a threaded interface for threadably interacting with a screw operatively connected with the actuator.

5. The fluid injector system of claim 1, wherein the actuator is at least one of a rotary electric motor, a linear electric motor, a linear actuator, and a solenoid.

6. The fluid injector system of claim 1, wherein rotational movement or linear movement of the actuator reversibly moves the cam sleeve axially in a direction along a longitudinal axis of the piston head.

7. A method for engaging a syringe plunger with a piston head of a fluid injector system, the method comprising:
   advancing the piston head at least partially into an interior cavity of the syringe plunger; and
   advancing a cam sleeve disposed in the piston head in an axial direction relative to the piston head,
   wherein the advancing of the cam sleeve causes one or more pins at least partially disposed in one or more tracks of the cam sleeve to move from a first, disengaged position, wherein the one or more pins are radially withdrawn into the piston head, to a second, engaged position, wherein the one or more pins protrude radially outward to engage at least a portion of the syringe plunger.

8. The method of claim 7, wherein the advancing of the cam sleeve relative to the piston head comprises rotating a screw operatively connected with a threaded interface of the cam sleeve.

9. The method of claim 7, further comprising engaging the one or more pins with a pin engagement surface on a portion of the syringe plunger when the one or more pins are in the second, engaged position.

10. A plunger engagement mechanism for a piston head of a fluid injector system, the plunger engagement mechanism comprising:
   a cam sleeve movable relative to the piston head, the cam sleeve having one or more tracks defining a cam surface;
   an actuator operatively connected to the cam sleeve for moving the cam sleeve relative to the piston head; and
   one or more pins at least partially disposed in and moveable within the one or more tracks of the cam sleeve,
   wherein movement of the cam sleeve causes movement of the one or pins within the one or more tracks, the one or more pins moveable between a first, disengaged position, wherein the one or more pins are radially withdrawn into the piston head, and a second, engaged position, wherein the one or more pins protrude radially outward relative to an outer surface of the piston head.

11. The plunger engagement mechanism of claim 10, wherein the piston head comprises one or more openings through which the one or more pins are movable between the first, disengaged position and the second, engaged position.

12. The plunger engagement mechanism of claim 10, wherein the one or more pins are configured to engage a pin engagement surface on a portion of a plunger when the one or more pins are in the second, engaged position.

13. The plunger engagement mechanism of claim 10, wherein the cam sleeve has a threaded interface for threadably interacting with a screw operatively connected with the actuator.

14. The plunger engagement mechanism of claim 13, wherein the threaded interface has a female thread or a male thread, and wherein the screw has a corresponding male thread or a corresponding female thread.

15. The plunger engagement mechanism of claim 10, wherein each of the one or more tracks diverge from a longitudinal axis of the piston head in a proximal to distal direction, such that a distal end of the track is radially farther from the longitudinal axis than a proximal end of the track.

16. The plunger engagement mechanism of claim 10, wherein each of the one or more pins has a bulbous end received in one of the one or more tracks.

17. The plunger engagement mechanism of claim 10, wherein each of the one or more tracks has a diagonally linear shape or an arcuate shape.

18. The plunger engagement mechanism of claim 10, wherein the actuator is a rotary electric motor, a linear electric motor, a linear actuator, or a solenoid.

19. The plunger engagement mechanism of claim 10, wherein rotational or linear movement of the actuator moves the cam sleeve in a linear direction.

20. The plunger engagement mechanism of claim 10, wherein the actuator is operatively connected to a controller for controlling rotary motion of the actuator.

\* \* \* \* \*

UNITED STATES PATENT AND TRADEMARK OFFICE
CERTIFICATE OF CORRECTION

PATENT NO. : 11,883,636 B2
APPLICATION NO. : 16/975944
DATED : January 30, 2024
INVENTOR(S) : Taheri et al.

It is certified that error appears in the above-identified patent and that said Letters Patent is hereby corrected as shown below:

In the Specification

In Column 8, Lines 17-18, delete "WO 2105/106,107" and insert -- WO 2015/106107 --, therefor.
In Column 8, Line 56, delete "FIG. B," and insert -- FIG. 1B, --, therefor.
In Column 9, Line 1, delete "B," and insert -- 1B, --, therefor.
In Column 15, Line 32, delete "can" and insert -- cam --, therefor.

Signed and Sealed this
Twenty-sixth Day of March, 2024

Katherine Kelly Vidal
*Director of the United States Patent and Trademark Office*